US008048628B2

(12) United States Patent
Pollack et al.

(10) Patent No.: US 8,048,628 B2
(45) Date of Patent: Nov. 1, 2011

(54) METHODS FOR NUCLEIC ACID AMPLIFICATION ON A PRINTED CIRCUIT BOARD

(75) Inventors: Michael G. Pollack, Durham, NC (US); Vamsee K. Pamula, Durham, NC (US); Richard B. Fair, Durham, NC (US)

(73) Assignee: Duke University, Durham, NC (US)

( * ) Notice: Subject to any disclaimer, the term of this patent is extended or adjusted under 35 U.S.C. 154(b) by 50 days.

(21) Appl. No.: 11/753,318

(22) Filed: May 24, 2007

(65) Prior Publication Data
US 2007/0217956 A1   Sep. 20, 2007

Related U.S. Application Data

(63) Continuation of application No. 11/343,284, filed on Jan. 30, 2006, which is a continuation-in-part of application No. 10/253,342, filed on Sep. 24, 2002, now Pat. No. 7,329,545.

(60) Provisional application No. 60/648,051, filed on Jan. 28, 2005.

(51) Int. Cl.
*C12Q 1/68* (2006.01)
*C12P 19/34* (2006.01)
(52) U.S. Cl. ...................... 435/6.12; 435/91.2
(58) Field of Classification Search ............ None
See application file for complete search history.

(56) References Cited

U.S. PATENT DOCUMENTS

| | | | |
|---|---|---|---|
| 3,872,480 A | 3/1975 | Engelbrecht | |
| 3,934,180 A | 1/1976 | Kiess et al. | |
| 4,390,403 A | 6/1983 | Batchelder | |
| 4,636,785 A | 1/1987 | Le Pesant | |
| 4,742,345 A | 5/1988 | Di Santo | |
| 4,818,052 A | 4/1989 | Le Pesant et al. | |
| 4,863,849 A | 9/1989 | Melamede | |
| 4,911,782 A | 3/1990 | Brown | |
| 5,181,016 A | 1/1993 | Lee | |
| 5,192,659 A | 3/1993 | Simons | |
| 5,240,994 A | 8/1993 | Brink et al. | |
| 5,276,125 A | 1/1994 | Pedain et al. | |
| 5,486,337 A | 1/1996 | Ohkawa | |
| 5,525,493 A | 6/1996 | Hornes et al. | |
| 5,757,345 A | 5/1998 | Sheridon | |
| 5,770,391 A | 6/1998 | Foote et al. | |
| 5,770,457 A | 6/1998 | Stocker et al. | |
| 5,777,391 A | 7/1998 | Nakamura et al. | |
| 5,808,593 A | 9/1998 | Sheridon | |
| 5,851,769 A | 12/1998 | Gray et al. | |
| 5,871,908 A | 2/1999 | Henco et al. | |
| 5,929,960 A | 7/1999 | West et al. | |
| 5,980,719 A | 11/1999 | Cherukuri et al. | |
| 5,994,056 A | 11/1999 | Higuchi | |
| 6,022,463 A | 2/2000 | Leader | |
| 6,106,685 A | 8/2000 | McBride et al. | |
| 6,171,785 B1 | 1/2001 | Higuchi et al. | |
| 6,210,891 B1 | 4/2001 | Nyren et al. | |
| 6,258,568 B1 | 7/2001 | Nyren | |
| 6,294,063 B1 | 9/2001 | Becker et al. | |
| 6,319,668 B1 | 11/2001 | Nova et al. | |
| 6,355,198 B1 | 3/2002 | Kim et al. | |
| 6,379,929 B1 | 4/2002 | Burns et al. | |
| 6,432,290 B1 | 8/2002 | Harrison et al. | |
| 6,473,492 B2 | 10/2002 | Prins | |
| 6,485,913 B1 | 11/2002 | Becker et al. | |
| 6,538,823 B2 | 3/2003 | Kroupenkine et al. | |
| 6,545,815 B2 | 4/2003 | Kroupenkine et al. | |
| 6,565,727 B1 | 5/2003 | Shenderov | |
| 6,586,233 B2 * | 7/2003 | Benett et al. ............... 435/286.5 |
| 6,596,238 B1 | 7/2003 | Belder et al. | |
| 6,600,888 B2 | 7/2003 | Mishra et al. | |
| 6,613,560 B1 | 9/2003 | Tso et al. | |
| 6,629,826 B2 | 10/2003 | Yoon et al. | |
| 6,661,563 B2 | 12/2003 | Hayashi et al. | |
| 6,665,127 B2 | 12/2003 | Bao et al. | |
| 6,692,700 B2 | 2/2004 | Handique | |
| 6,767,706 B2 | 7/2004 | Quake et al. | |
| 6,773,566 B2 | 8/2004 | Shenderov | |
| 6,814,934 B1 | 11/2004 | Higuchi | |
| 6,828,100 B1 | 12/2004 | Ronaghi | |
| 6,841,128 B2 | 1/2005 | Kambara et al. | |
| 6,893,547 B2 | 5/2005 | Gascoyne et al. | |
| 6,897,848 B2 | 5/2005 | Sheridon | |
| 6,911,132 B2 | 6/2005 | Pamula et al. | |

(Continued)

FOREIGN PATENT DOCUMENTS

DE      3808942 A1      9/1989

(Continued)

OTHER PUBLICATIONS

Pollack et al., "Investigation of Electrowetting-based microfluidics for real-time PCR applications," 7th Int'l Conference on Micro Total Analysis Systems (uTAS), 2003, p. 1-4.*
Cooney et al., "Isothermal DNA Amplification Reaction on an Electrowetting Microchip," Keck Graduate Institute online poster publication (http://microfluidics.kgi.edu/publications/ACS-sandiego-poster-2004.pdf), 2004, p. 1.*
Paik et al., "Thermal Effects on Droplet Transport in Digital Microfluidics with Applications to Chip Cooling," Inter Society Conference on Thermal Phenomena, 2004, p. 649-654.*
Wang et al., "Droplet-based micro oscillating-flow PCR chip," J. Micromech. and Microeng., 2005, vol. 15, pp. 1369-1377.*
Zhang et al., "Behaviorial Modeling and Performance Evaluation of Microelectrofluidics-Based PCR Systems using SystemC," IEEE, 2004, vol. 23, No. 6, pp. 843-858.*
Gong et al., "Two-Dimensional Digital Microfluidic System by Multi-Layer Printed Circuit Board," IEEE, 2005, pp. 726-729.*
Zou et al., "Micro-assembled multi-chamber thermal cycler for low-cost reaction chip thermal multiplexing," Sens. and Actuat., 2002, vol. 102, pp. 114-121.*

(Continued)

*Primary Examiner* — Kenneth R. Horlick
(74) *Attorney, Agent, or Firm* — William A. Barrett; Ward and Smith, P.A.

(57) ABSTRACT

Methods for amplifying nucleic acid, such as DNA or RNA, on a printed circuit board (PCB) substrate are disclosed. The amplification can be achieved through a variety of methods such as thermocycling or isothermally. The printed circuit board substrate can comprise an array of electrodes for transporting droplets and can be part of a sandwich structure including a top plate parallel to the printed circuit board substrate.

1 Claim, 11 Drawing Sheets

U.S. PATENT DOCUMENTS

| | | | |
|---|---|---|---|
| 6,949,176 B2 | 9/2005 | Vacca et al. | |
| 6,958,132 B2 | 10/2005 | Chiou et al. | |
| 6,989,234 B2 | 1/2006 | Kolar et al. | |
| 7,167,156 B1 | 1/2007 | Glass | |
| 7,183,509 B2 | 2/2007 | Beerling | |
| 7,329,545 B2 | 2/2008 | Pamula et al. | |
| 7,439,014 B2 | 10/2008 | Pamula et al. | |
| 7,687,280 B2 | 3/2010 | Woudenberg et al. | |
| 7,833,711 B2 | 11/2010 | Woudenberg et al. | |
| 7,833,719 B2 | 11/2010 | O'Keefe et al. | |
| 7,888,108 B2 | 2/2011 | Woudenberg et al. | |
| 2002/0043463 A1 | 4/2002 | Shenderov | |
| 2002/0058332 A1 | 5/2002 | Quake et al. | |
| 2002/0093651 A1 | 7/2002 | Roe | |
| 2002/0100612 A1 | 8/2002 | Crockett et al. | |
| 2002/0125135 A1 | 9/2002 | Derand et al. | |
| 2002/0128546 A1 | 9/2002 | Silver | |
| 2002/0168671 A1* | 11/2002 | Burns et al. | 435/6 |
| 2002/0172969 A1 | 11/2002 | Burns et al. | |
| 2003/0006140 A1 | 1/2003 | Vacca et al. | |
| 2003/0012483 A1 | 1/2003 | Ticknor et al. | |
| 2003/0012699 A1 | 1/2003 | Moore et al. | |
| 2003/0082081 A1 | 5/2003 | Fouillet et al. | |
| 2003/0103021 A1 | 6/2003 | Young et al. | |
| 2003/0119057 A1 | 6/2003 | Gascoyne et al. | |
| 2003/0164295 A1 | 9/2003 | Sterling | |
| 2003/0175947 A1* | 9/2003 | Liu et al. | 435/288.5 |
| 2003/0175990 A1 | 9/2003 | Hayenga et al. | |
| 2003/0183525 A1 | 10/2003 | Elrod et al. | |
| 2003/0205632 A1 | 11/2003 | Kim et al. | |
| 2003/0206351 A1 | 11/2003 | Kroupenkine | |
| 2003/0224528 A1 | 12/2003 | Chiou et al. | |
| 2003/0227100 A1 | 12/2003 | Chandross et al. | |
| 2004/0007377 A1 | 1/2004 | Fouillet et al. | |
| 2004/0031688 A1 | 2/2004 | Shenderov | |
| 2004/0042721 A1 | 3/2004 | Kroupenkine et al. | |
| 2004/0053290 A1 | 3/2004 | Terbrueggen et al. | |
| 2004/0055536 A1 | 3/2004 | Kolar et al. | |
| 2004/0055891 A1 | 3/2004 | Pamula et al. | |
| 2004/0058450 A1 | 3/2004 | Pamula et al. | |
| 2004/0091392 A1 | 5/2004 | McBridge et al. | |
| 2004/0136876 A1 | 7/2004 | Fouillet et al. | |
| 2004/0141884 A1 | 7/2004 | Unno et al. | |
| 2004/0211659 A1 | 10/2004 | Velev | |
| 2004/0231987 A1 | 11/2004 | Sterling et al. | |
| 2006/0132543 A1 | 6/2006 | Elrod et al. | |
| 2006/0194331 A1 | 8/2006 | Pamula et al. | |
| 2006/0254933 A1 | 11/2006 | Adachi et al. | |
| 2007/0023292 A1* | 2/2007 | Kim et al. | 204/643 |
| 2007/0115308 A1 | 5/2007 | Hisano et al. | |
| 2007/0196237 A1* | 8/2007 | Neuzil et al. | 422/67 |
| 2008/0138815 A1 | 6/2008 | Brown et al. | |
| 2008/0153091 A1 | 6/2008 | Brown et al. | |
| 2008/0160525 A1 | 7/2008 | Brown et al. | |
| 2008/0169184 A1 | 7/2008 | Brown et al. | |
| 2008/0171324 A1 | 7/2008 | Brown et al. | |
| 2008/0171325 A1 | 7/2008 | Brown et al. | |
| 2008/0171326 A1 | 7/2008 | Brown et al. | |
| 2008/0171327 A1 | 7/2008 | Brown et al. | |
| 2008/0171382 A1 | 7/2008 | Brown et al. | |
| 2008/0213766 A1 | 9/2008 | Brown et al. | |
| 2009/0134009 A1 | 5/2009 | Roux et al. | |
| 2011/0003281 A1 | 1/2011 | Woudenberg et al. | |
| 2011/0065590 A1 | 3/2011 | Hunter | |

FOREIGN PATENT DOCUMENTS

| | | |
|---|---|---|
| DE | 10162188 A1 | 6/2003 |
| EP | 0676643 A | 10/1995 |
| WO | WO9015881 | 12/1990 |
| WO | 9822625 A1 | 5/1998 |
| WO | 9915876 A1 | 4/1999 |
| WO | WO9917093 A1 | 4/1999 |
| WO | WO9954730 A1 | 10/1999 |
| WO | 03069380 A1 | 8/2003 |
| WO | 2004027490 A1 | 4/2004 |

OTHER PUBLICATIONS

Pollack et al., "Electrowetting-based actuation of droplets for integrated microfluidics," Lab Chip, 2002, vol. 2, pp. 96-101.*
Fair et al., "Electrowetting-Based On-Chip Sample Processing for Integrated Microfluidics," IEEE Inter. Electron Devices Meeting (IEDM), 2003, pp. 1-4.*
Shen et al., "A microchip-based PCR device using flexible printed circuit technology," Sens. and Actuat., 2005, vol. 105, pp. 251-258.*
PCT International Preliminary Report on Patentability for PCT/US06/003230 dated Sep. 25, 2007.
PCT International Search Report and Written Opinion for PCT/US06/003230 dated Aug. 29, 2007.
Cho et al., "Towards Digital Microfluidic Circuits: Creating, Transporting, Cutting and Merging Liquid Droplets by Electrowetting-Based Actuation," Proc. IEEE/Micro Electro Mechanical Systems Conference, pp. 32-35, 2002.
Juergen Pipper et al., "Clockwork PCR Including Sample Preparation," Angew. Chem. Int. Ed., vol. 47, pp. 3900-3904, 2008.
Olivier Raccurt et al., "On the influence of surfactants in electrowetting systems," J. Micromech. Microeng., vol. 17, pp. 2217-2223 (2007).
Jean-Maxime Roux and Yves Fouillet, "3D droplet displacement in microfluidic systems by electrostatic actuation," Sensors and Actuators A, vol. 134, Issue 2, pp. 486-493, Mar. 15, 2007.
Seyrat E, Hayes RA, "Amorphous fluoropolymers as insulators for reversible low-voltage electrowetting," Journal of Applied Physics, vol. 90 (3): pp. 1383-1386, Aug 1, 2001.
Masao Washizu, "Electrostatic Actuation of Liquid Droplets for Micro-Reactor Applications", IEEE Industry Applications Society Annual Meeting, pp. 1867-1873, Oct. 5-9, 1997.
Aaron R. Wheeler, "Putting Electrowetting to Work," Science, vol. 322, No. 5901, pp. 539-540, Oct. 24, 2008.
European Search Report for EP 06734056.2 dated Jan. 28, 2008.
"Chip mixes droplets faster", MIT Technology Review, Oct. 2003.
"Chip Juggles Droplets", Technology Research News, Sep. 4-11, 2002.
"Laboratory on a Chip", Popular Mechanics, Mar. 2002.
"Lab-on-a-Chip Technology May Present New ESD Challenges", Electrostatic Discharge Journal, Mar. 2002.
"Making materials fit the future: accommodating relentless technological requirements means researchers must recreate and reconfigure materials, frequently challenging established laws of physics, while keeping an eye on Moore's law", R&D Magazine, Dec. 2001.
Ali Agah, "DNA Analysis Chip by Electrowetting Actuation," Stanford Nanofabrication Facility, p. 9, 2002.
L. Altomare, M. Borgatti, G. Medoro, M. Manaresi, M. Tartagni, R. Guerrieri and R. Gambari, "Levitation and Movement of Human Tumor Cells Using a Printed Circuit Board Device Based on Software-Controlled Dielectrophoresis", Biotechnology and Bioengineering, vol. 82, pp. 474-479 (2003).
B. Berge and J. Peseux, "Variable focal lens controlled by an external voltage: An application of electrowetting," The European Physical Journal E, vol. 3, pp. 159-163 (2000).
Bhansali et al., "Resolving chemical/bio-compatibility issues in microfluidic MEMS systems," SPIE Conference on Microfluidic Devices and Systems II, vol. 3877, Santa Clara, CA, pp. 101-109 (1999).
Dewey A, Srinivasan V, Icoz E, "Visual modeling and design of microelectromechanical system transducers", Microelectronics Journal, vol. 32, pp. 373-381, Apr. 2001.
Dewey A, Srinivasan V, Icoz E, "Towards a visual modeling approach to designing micro electromechanical system transducers," Journal of Micromechanics and Microengineering, vol. 9, pp. 332-340, Dec. 1999.
R.B. Fair, A. Khlystov, V. Srinivasan, V. K. Pamula, K.N. Weaver, "Integrated chemical/biochemical sample collection, pre-concentration, and analysis on a digital microfluidic lab-on-a-chip platform," Lab-on-a-Chip: Platforms, Devices, and Applications, Conf. 5591, SPIE Optics East, Philadelphia, Oct. 25-28, 2004.
Jian Gong et al., "Portable digital microfluidics platform with active but disposable Lab-On-Chip," Micro Electro Mechanical Systems, 17th IEEE International Conference on (MEMS), Maastricht, Netherlands, Jan. 25-29, 2004; Piscataway, NJ, IEEE, Jan. 25, 2004, pp. 355-358.

Ying Huang et al., "MEMS-based sample preparation for molecular diagnostics", Analytical and Bioanalytical Chemistry, vol. 372, pp. 49-65 (2002).

G. Jobst, I. Moser, P. Svasek, M. Varahram, Z. Trajanoski, P. Wach, P. Kotanko, F. Skrabal, and G. Urban, "Mass producible miniaturized flow through a device with a biosensor array," Sensors and Actuators B-Chemical, vol. 43, pp. 121-125 (Sep. 1997).

C. Laritz and L. Pagel, "A microfluidic pH-regulation system based on printed circuit board technology," Sensors and Actuators A-Physical, vol. 84, No. 3, pp. 230-235 (Sep. 1, 2000).

G. Medoro, N. Manaresi, A. Leonardi, L. Altomare, M. Tartagni and R. Guerrieri, "A Lab-on-a-Chip for Cell Detection and Manipulation", IEEE Sensors Journal, vol. 3, pp. 317-325 (2003).

T. Merkel, L. Pagel, and H.W. Glock, "Electric fields in fluidic channels and sensor applications with capacitance," Sensors and Actuators A, vol. 80, pp. 1-7 Mar. 1, 2000.

T. Merkel, M. Graeber, and L. Pagel, "A new technology for fluidic microsystems based on PCB technology," Sensors and Actuators A-Physical, vol. 77, No. 2, pp. 98-105 (Oct. 12, 1999).

N.T. Nguyen and X.Y. Huang, "Miniature valveless pumps based on printed circuit board technique," Sensors and Actuators A-Physical, vol. 88, No. 2, pp. 104-111 (Feb. 15, 2001).

Paik et al., "Coplanar Digital Microfluidics Using Standard Printed Circuit Board Processes," 9th International Conference on Miniaturized Systems for Chemistry and Lice Sciences (MicroTAS), pp. 566-568, Oct. 2005.

Paik et al., "Coplanar Digital Microfluidics Using Standard Printed Circuit Board Processes," 9th International Conference on Miniaturized Systems for Chemistry and Lice Sciences (MicroTAS) Poster, Oct. 2005.

Phil Paik, Vamsee K. Pamula, Michael G. Pollack and Richard B. Fair, "Electrowetting-based droplet mixers for microfluidic systems", Lab on a Chip (LOC), vol. 3, pp. 28-33, 2003.

Phil Paik, Vamsee K. Pamula, and Richard B. Fair, "Rapid droplet mixers for digital microfluidic systems," Lab on a Chip (LOC), vol. 3, pp. 253-259, 2003.

V.K. Pamula, V. V Srinivasan, H. Chakrapani, R.B. Fair, E.J. Toone, "A droplet-based lab-on-a-chip for colorimetric detection of nitroaromatic explosives," Proceedings of Micro Electro Mechanical Systems, pp. 722-725, 2005.

Vamsee K. Pamula and Krishnendu Chakrabarty, "Cooling of integrated circuits using droplet-based microfluidics," Proc. ACM Great Lakes Symposium on VLSI, pp. 84-87, Apr. 2003.

Pollack et al., "Electrowetting-based actuation of liquid droplets for microfluidic applications," Appl. Phys. Letters, vol. 77, No. 1 (Sep. 11, 2000), pp. 1725-1726.

Pollack et al., "Electrowetting-Based Microfluidics for High-Throughput Screening," smallTalk2001 Conference Program Abstract (Aug. 2001), p. 149, San Diego.

Prins et al., "Fluid Control in Multichannel Structures by Electrocapillary Pressure," Science vol. 291, pp. 277-280, Jan. 12, 2001.

Hong Ren, Vijay Srinivasan, Michael G. Pollack, and Richard B. Fair, "Automated electrowetting-based droplet dispensing with good reproducibility," Proc. Micro Total Analysis Systems (mTAS), pp. 993-996, 2003.

Hong Ren, Vijay Srinivasan, and Richard B. Fair, "Design and testing of an interpolating mixing architecture for electrowetting-based droplet-on-chip chemical dilution", Transducers 2003, pp. 619-622, 2003.

Vijay Srinivasan, Vamsee K. Pamula, Michael G. Pollack, and Richard B. Fair, "A digital microfluidic biosensor for multianalyte detection", Proc. IEEE 16th Micro Electro Mechanical Systems Conference, pp. 327-330, 2003.

Vijay Srinivasan, Vamsee K. Pamula, Richard B. Fair, "An integrated digital microfluidic lab-on-a-chip for clinical diagnostics on human physiological fluids," Lab on a Chip (LOC), vol. 4, pp. 310-315, 2004.

Vijay Srinivasan, Vamsee K. Pamula, Michael G. Pollack, and Richard B. Fair, "Clinical diagnostics on human whole blood, plasma, serum, urine, saliva, sweat, and tears on a digital microfluidic platform," Proc. Micro Total Analysis Systems (mTAS), pp. 1287-1290, 2003.

Vijay Srinivasan, Vamsee K. Pamula, Richard B. Fair, "Droplet-based microfluidic lab-on-a-chip for glucose detection," Analytica Chimica Acta, vol. 507, No. 1, pp. 145-150, 2004.

V. Srinivasan, V.K. Pamula, P. Paik, and R.B. Fair, "Protein Stamping for MALDI Mass Spectrometry Using an Electrowetting-based Microfluidic Platform," Lab-on-a-Chip: Platforms, Devices, and Applications, Conf. 5591, SPIE Optics East, Philadelphia, Oct. 25-28, 2004.

Vijay Srinivasan, Anand Jog and Richard B. Fair, "Scalable Macromodels for Microelectromechanical Systems," Technical Proc. 2001 Int. Conf. on Modeling and Simulation of Microsystems, pp. 72-75, 2001.

Vijay Srinivasan, Vamsee K. Pamula, K. Divakar Rao, Michael G. Pollack, Joseph A. Izatt, and Richard B. Fair, "3-D imaging of moving droplets for microfluidics using optical coherence tomography," Proc. Micro Total Analysis Systems (mTAS), pp. 1303-1306, 2003.

F. Su, S. Ozev and K. Chakrabarty, "Testing of droplet-based microelectrofluidic systems", Proc. IEEE International Test Conference, pp. 1192-1200, 2003.

A. P. Sudarsan and V.M. Ugaz, "Printed circuit technology for fabrication of plastic based microfluidic devices," Analytical Chemistry vol. 76, No. 11, pp. 3229-3235 (Jun. 1, 2004).

T. Taniguchi et al., "Chemical reactions in microdroplets by electrostatic manipulation of droplets in liquid media," Lab on a Chip, vol. 2, No. 2, pp. 19-23 (2002).

Altti Torkkeli, "Droplet microfluidics on a planar surface," Doctoral Dissertation, Department of Electrical Engineering, Helsinki University of Technology (Oct. 3, 2003).

E. Verpoorte, "Beads and chips: new recipes for analysis," Lab on a Chip (LOC), vol. 3, pp. 60N-68N, 2003.

A. Wego, H.W. Glock, L Pagel, and S. Richter, "Investigations on thermo-pneumatic volume actuators based on PCB technology," Sensors and Actuators A-Physical, vol. 93, No. 2, pp. 95-102 (Sep. 30, 2001).

A. Wego and L. Pagel, "A self-filling micropump based on PCB technology," Sensors and Actuators A-Physical, vol. 88, No. 3, pp. 220-226 (Mar. 5, 2001).

A.R. Wheeler, H. Moon, C.A. Bird, R.R. Loo, C.J. Kim, J.A. Loo, R.L. Garrell, "Digital microfluidics with in-line sample purification for proteomics analyses with MALDI-MS," Analytical Chemistry, vol. 77, No. 2, pp. 534-540 (Jan. 15, 2005).

Wheeler et al., "Electrowetting-on-dielectric for analysis of peptides and proteins by matrix assisted laser desorption/ionization mass spectrometry," Solid-State Sensor, Actuator and Microsystems Workshop publication, pp. 402-403, Jun. 6-10, 2004.

M. Yamaguchi et al., "High-Throughput Method for N-Terminal Sequencing of Proteins by MALDI Mass Spectrometry," Analytical Chemistry, vol. 77, No. 2, pp. 645-651 (Jan. 15, 2005).

Yi et al., "Geometric surface modification of nozzles for complete transfer of liquid drops," Solid-State Sensor, Actuator and Microsystems Workshop, pp. 164-167, Jun. 6-10, 2004.

Michael Armani et al., "Control of Microfluidic Systems: Two Examples, Results, and Challenges," International Journal of Robust and Nonlinear Control, vol. 15, Issue 16, pp. 785-803, Sep. 15, 2005.

Shih-Kang Fan et al., "EWOD Driving of Droplet on NxM Grid Using Single-Layer Electrode Patterns," Solid-State Sensor, Actuator and Microsystems Workshop, Hilton Head Island, South Carolina, pp. 134-137, Jun. 2-6, 2002.

A. Wego, S. Richter, L. Pagel, "Fluidic microsystems based on printed circuit board technology," Journal of Micromechanics and Microengineering, vol. 11, No. 5, pp. 528-531 (Sep. 2001).

Hung-Pin Chang, et al., "Low Cost RF MEMS Switches Fabricated on Microwave Laminate Printed Circuit Boards," Department of Electrical and Computer Engineering, University of California at Irvine, Irvine, CA, 92697, USA Integrated Nanosystems Research Facility, University of California at Irvine, Irvine, CA, 92697, pp. 1-4, Apr. 2003.

Chatterjee, Debalina. "Lab on a Chip Applications with a Digital Microfluidic Platform," UCLA Dissertation 2008, UMI Microform No. 3342975.

Gong, Jian et al., Declaration Under 37 CFR 1.131, filed in the USPTO Aug. 20, 2010 in U.S. Appl. No. 11/460,188, filed Jul. 26, 2006, entitled "Small Object Moving on Printed Circuit Board".

Nicole Weaver, "Application of Magnetic Microspheres for Pyrosequencing on a Digital Microfluidic Platform," web publication, Aug. 29, 2005.

Li Cheuk-Wing et al., Development of PDMS-based Microfluid Device for Cell-based Assays; Applied Research Centre for Genomic Technology, and Department of Biology and Chemistry, Chemical Journal of Chinese Universities, vol. 25, Apr. 2004, Suppl. pp. 4-6.

Jie Ding, "System level architectural optimization of semi-reconfigurable microfluidic system," M.S. Thesis, Duke University Dept of Electrical Engineering, 2000.

C.W. Li, C.N. Cheung, J. Yang, C.H. Tzang, and M.S. Yang, "PDMS-based microfluidic device with multi-height structures fabricated by single-step photolithography using printed circuit board as masters," Analyst, vol. 128, No. 9, pp. 1137-1142 (2003).

Moon, Hyejin, Ph.D., "Electrowetting-on-dielectric microfluidics: Modeling, physics, and MALDI application," University of California, Los Angeles, 2005, 122 Pages.

J.A. Schwartz, "Dielectrophoretic Approaches to Sample Preparation and Analysis," The University of Texas, Dissertation, Dec. 2001.

J.A. Schwartz, J.V. Vykoukal and P.R.C. Gascoyne, "Droplet-based chemistry on a programmable micro-chip," Lab on a Chip, vol. 4, No. 1, pp. 11-17 (2002).

Y. Tan, J.S. Fisher, A.I. Lee, V. Cristini and A. P. Lee, "Design of microfluidic channel geometries for the control of droplet volume, chemical concentration, and sorting," Lab on a Chip, vol. 4, No. 4, pp. 292-298 (2004).

J.D. Tice, A.D. Lyon, and R.F. Ismagilov, "Effects of viscosity on droplet formation and mixing in microfluidic channels," Analytica Chimica Acta, vol. 507, pp. 73-77 (2004).

M.A. Unger, H.P. Chou, T. Thorsen, A. Scherer, S.R. Quake, "Monolithic Microfabricated Valves and Pumps by Multilayer Soft Lithography," Science, vol. 288, pp. 113-116 (2000).

Colgate E, Matsumoto H, "An Investigation of Electrowetting-based Microactuation," Journal of Vacuum Science & Technology A—Vacuume Surfaces and Films, V. 8 (4): pp. 3625-3633, Jul.-Aug. 1990.

Shih-Kang Fan, "Digital Microfluidics by Cross-Reference EWOD Actuation: Principle, Device, and System," PhD Dissertation, University of California Dept. of Mechanical Engineering, 2003.

Fowler, Steve, "Lab-on-a-Chip Technology May Present New ESD Challenges", Electrostatic Discharge (ESD) Journal, Mar. 2002.

Kim, Chang-Jin et al., "U.S. Appl. No. 10/343,261 Electrowetting-Driven Micropumping," UCLA Invention Report, Amendment, Declaration including Invention Report, Petition for Extension of Time, and Authorization to Charge Deposit, submitted to USPTO on Feb. 4, 2005.

Kim, Chang-Jin et al., "U.S. Appl. No. 11/460,188 Small Object Moving on Printed Circuit Board", Declaration under 37 CFR 1.131, UCLA invention disclosure exhibits, Jul. 26, 2006.

Kuzmin et al., Mol Gen Mikrobiol Virusol, 1991, vol. 8, pp. 6-8.

Pollack et al., "Investigation of electrowetting-based microfluidics for real-time PCR applications," 7th Int'l Conference on Micro Total Analysis Systems (μTAS) 2003.

Terry, S.C., J.H. Jerman, and J.B. Angell, "A Gas Chromatographic Air Analyzer Fabricated on a Silicon Wafer," IEEE Transactions on Electron Devices, vol. ED-26, 1979, pp. 1880-1886.

Tuckerman, D.B. and R.F.W. Pease, "High-Performance Heat Sinking for VLSI,"IEEE Electron Device Letters, 1981, pp. 126-129.

Batchelder, J.S., "Dielectrophoretic manipulator," Review of Scientific Instruments, vol. 54, 1983, pp. 300-302.

Manz, A., N. Graber, and H.M. Widmer, "Miniaturized Total Chemical Analysis Systems: a Novel Concept for Chemical Sensing," Sensors and Actuators B: Chemical, 1990, pp. 244-248.

Welters, W.J.J. and L.G.J. Fokkink, "Fast Electrically Switchable Capillary Effects," Langmuir, vol. 14, Mar. 1998, pp. 1535-1538.

McDonald, J.C., D.C. Duffy, J.R. Anderson, D.T. Chiu, H. Wu, O.J.A. Schuueller, and G.M. Whitesides, "Fabrication of Microfluidic systems in poly (dimethylsiloxane)," Electrophoresis, vol. 21, 2000, pp. 27-40.

Moon H, Cho SK, Garrell RL, et al., "Low voltage electrowetting-on-dielectric," Journal of Applied Physics, vol. 92 (7): pp. 4080-4087, Oct. 1, 2002.

Locascio, L.E., et al. "Polymer microfluidic devices," Talanta, vol. 56, Feb. 2002, pp. 267-287.

Garrell, R.L. et al., "Preventing Biomolecular Adsorption in Electrowetting-Based Biofluidic Chips," Analytical Chemistry, vol. 75, Oct. 2003, pp. 5097-5102.

P.Y. Chiou, H. Moon, H. Toshiyoshi, C.-J. Kim, and M.C. Wu, "Light actuation of liquid by optoelectrowetting," Sensors and Actuators A: Physical, vol. 104, May 2003, pp. 222-228.

Squires, T.M. and S.R. Quake, "Microfluidics: Fluid physics at the nanoliter scale," Reviews of Modern Physics, vol. 77, Oct. 2005, pp. 977-1-26.

Fouillet, Y., D. Jary, A.G. Brachet, C. Chabrol, J. Boutet, P. Clementz, R. Charles, and C. Peponnet, "Design and Validation of a Complex Generic Fluidic Microprocessor Based on EWOD Droplet for Biological Applications," 9th International Conference on Miniaturized Systems for Chemistry and Life Sciences (MicroTAS), Boston, MA: 2005, pp. 58-60.

Z. Guttenberg, H. Muller, H. Habermuller, A. Geisbauer, J. Pipper, J. Felbel, M. Kielpinski, J. Scriba, and A. Wixforth, "Planar chip devices for PCR and hybridization with surface acoustic wave pump.," Lab on a chip, vol. 5, Mar. 2005, pp. 12617-12622.

Yager, P., T. Edwards, E. Fu, K. Helton, K. Nelson, M.R. Tam, and B.H. Weigl, "Microfluidic diagnostic technologies for global public health," Nature, vol. 442, 2006, pp. 412-418.

Cooney, C.G., C-Y. Chen, M.R. Emerling, A Nadim, and J.D. Sterling, Microfluidics and Nanofluidics, vol. 2 Mar. 2006, pp. 435-446.

Chatterjee, D., B. Hetayothin, A.R. Wheeler, D.J. King, and R.L. Garrell, "Droplet-based microfluidics with nonaqueous solvents and solutions.," Lab on a Chip, vol. 6, Feb. 2006, pp. 199-206.

M.Madou, J. Zoval, G. Jia, H. Kido, J. Kim, "Lab on a CD," Annual Review of Biomedical Engineering, vol. 8, pp. 601-628, 2006.

Yi, U.-C. and C.-J. Kim, " Characterization of electrowetting actuation on addressable single-side coplanar electrodes," Journal of Micromechanics and Microengineering, vol. 16, Oct. 2006, pp. 2053-2059.

Dubois, P., G. Marchand, Y. Fouillet, J. Berthier, T. Douki, F. Hassine, S. Gmouh, and M. Vaultier, "Ionic Liquid Droplet as e-Microreactor," Analytical Chemistry, vol. 78, 2006, pp. 4909-4917.

Whitesides, G.M., "The origins and the future of microfluidics," Nature, vol. 442, 2006, pp. 368-373.

Chin, C.D., V. Linder, and S.K. Sia, "Lab-on-a-chip devices for global health: past studies and future opportunities.," Lab on a Chip, vol. 7, Jan. 2007, pp. 41-57.

Baviere, R., J. Boutet, and Y. Fouillet, "Dynamics of droplet transport induced by electrowetting actuation," Microfluidics and Nanofluidics, vol. 4, May 2007, pp. 287-294.

Office Action dated Oct. 7, 2009 from co-pending U.S. Appl. No. 11/343,284.

Response to Office Action dated Oct. 14, 2009 from co-pending U.S. Appl. No. 11/343,284.

Office Action dated Jan. 27, 2010 from co-pending U.S. Appl. No. 11/343,284.

Response to Office Action dated Jan. 29, 2010 from co-pending U.S. Appl. No. 11/343,284.

Office Action dated Jan. 25, 2011 from co-pending U.S. Appl. No. 11/343,284.

Response to Office Action dated Jan. 28, 2011 from co-pending U.S. Appl. No. 11/343,284.

Office Action dated Jun. 9, 2011 from co-pending U.S. Appl. No. 11/343,284.

Office Action dated Aug. 20, 2010 from co-pending U.S. Appl. No. 12/576,794.

Response to Office Action dated Nov. 4, 2010 from co-pending U.S. Appl. No. 12/576,794.

Office Action dated Dec. 23, 2010 from co-pending U.S. Appl. No. 12/576,794.

Response to Office Action dated Jan. 17, 2011 from co-pending U.S. Appl. No. 12/576,794.
Office Action dated Feb. 9, 2011 from co-pending U.S. Appl. No. 12/576,794.
Response to Office Action dated Apr. 7, 2011 from co-pending U.S. Appl. No. 12/576,794.
Response to Office Action dated Apr. 28, 2011 from co-pending U.S. Appl. No. 12/576,794.
Response to Office Action dated May 19, 2011 from co-pending U.S. Appl. No. 12/576,794.
Lee J, Kim CJ, "Surface-tension-driven microactuation based on continuous electrowetting," Journal of Microelectromechanical Systems, vol. 9 (2): pp. 171-180, Jun. 2000.

* cited by examiner

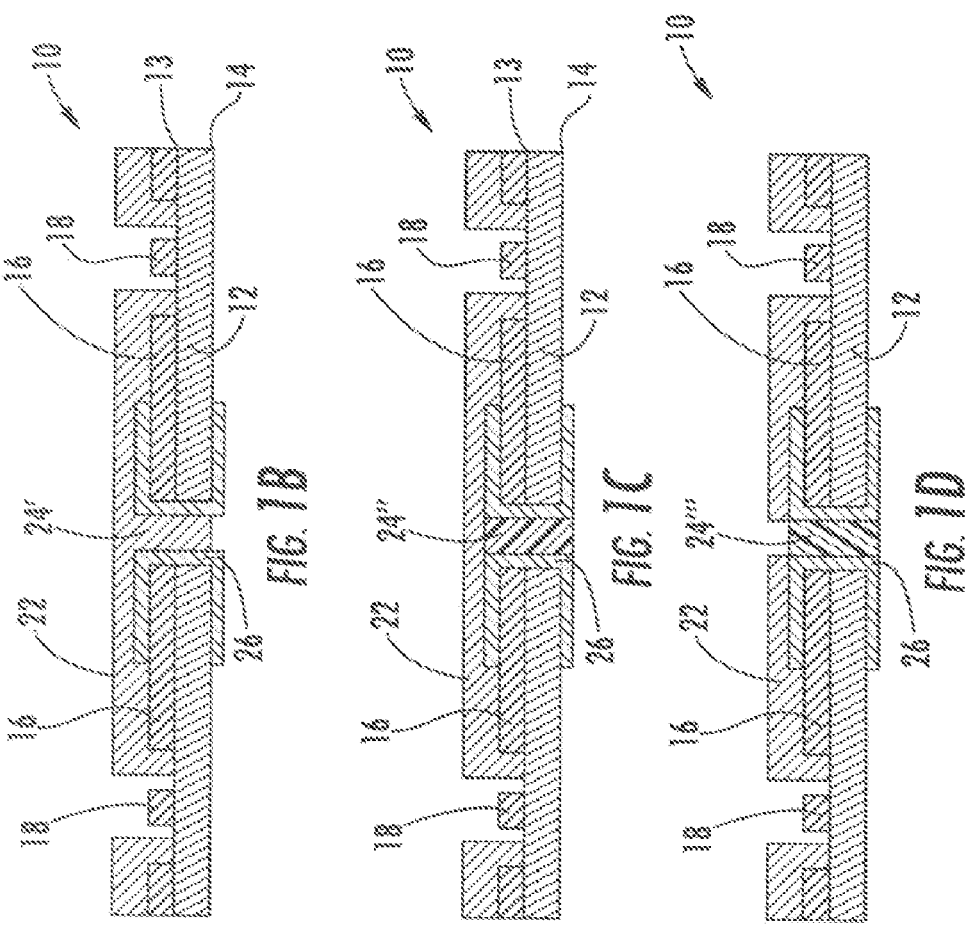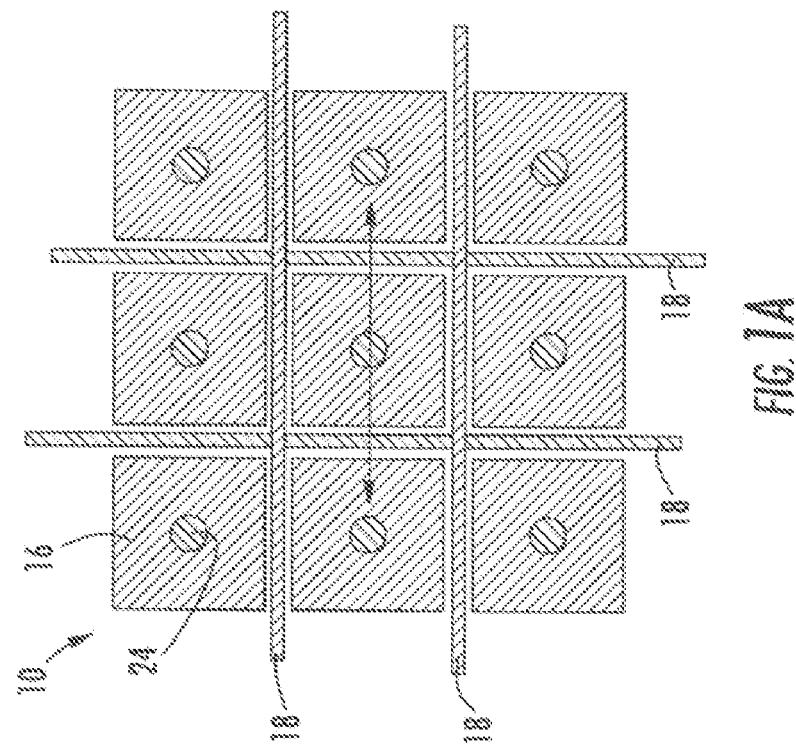

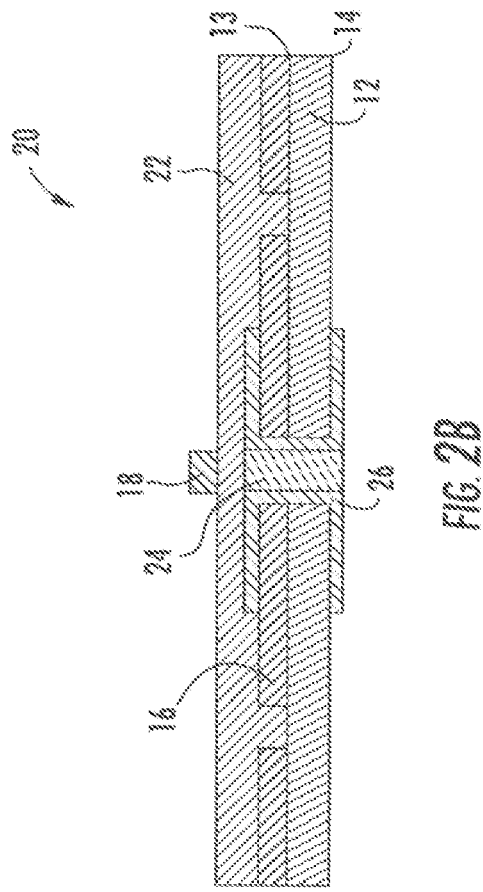
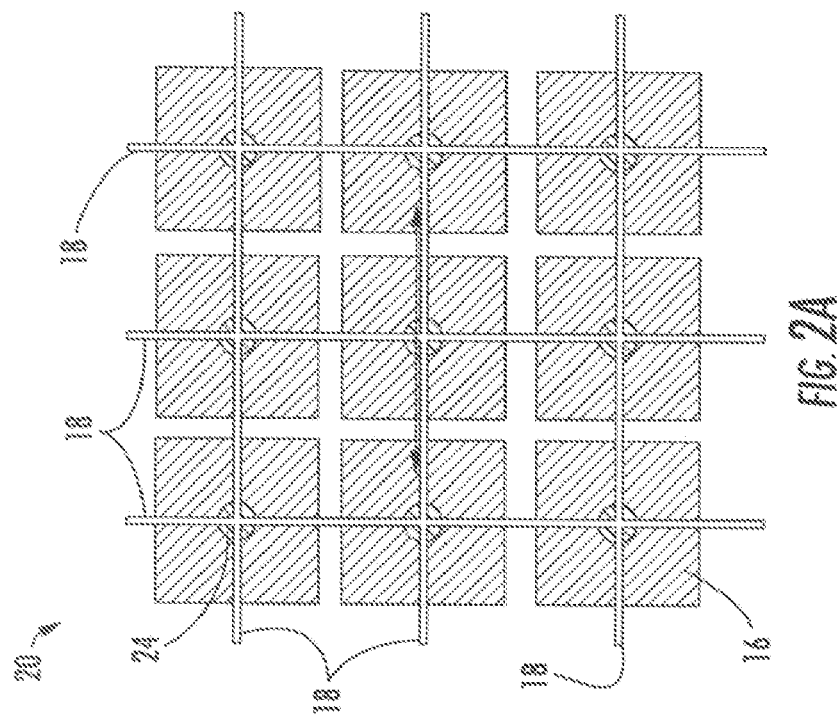

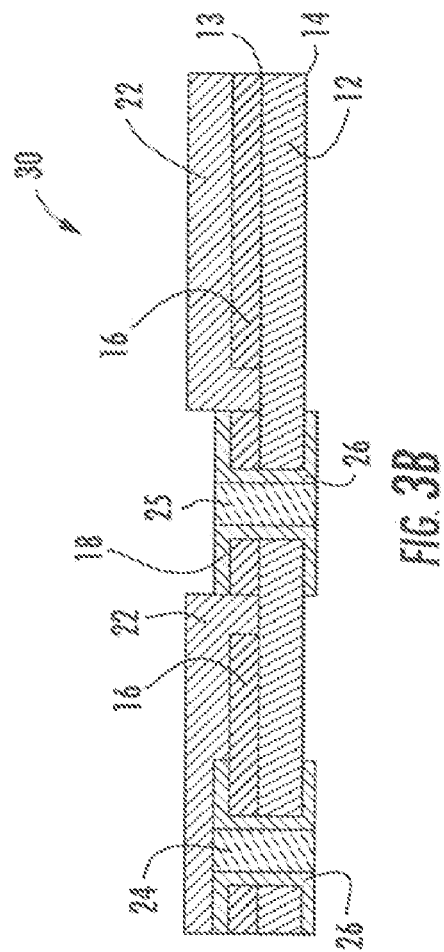
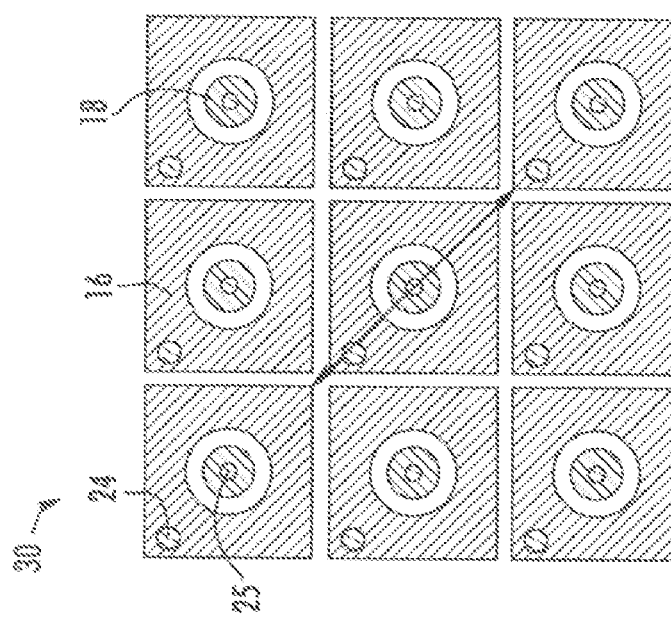

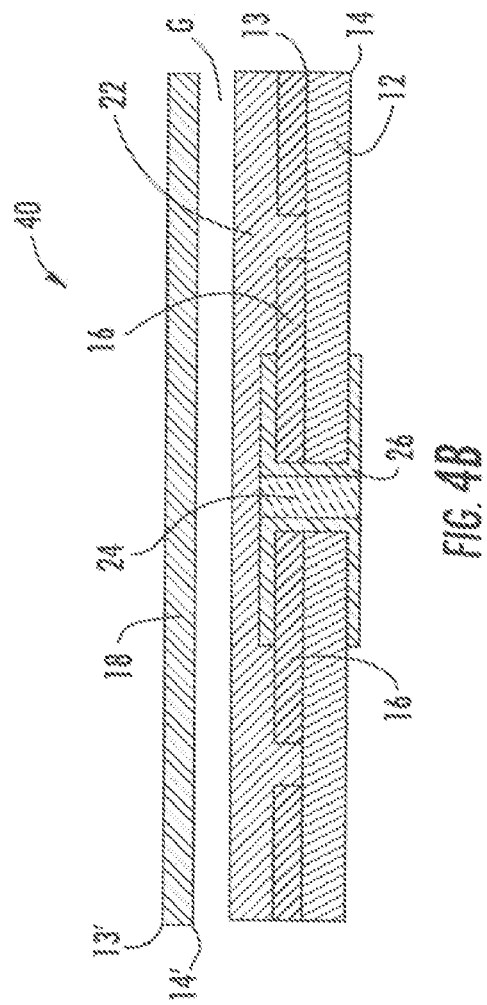
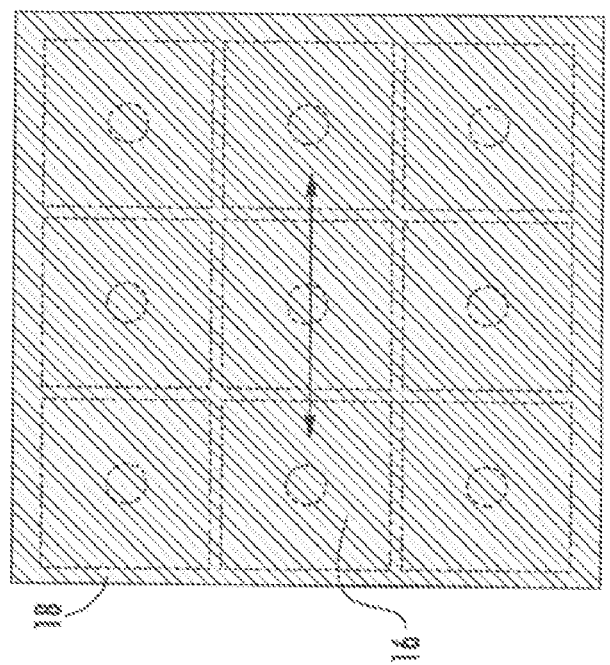
FIG. 4B
FIG. 4A

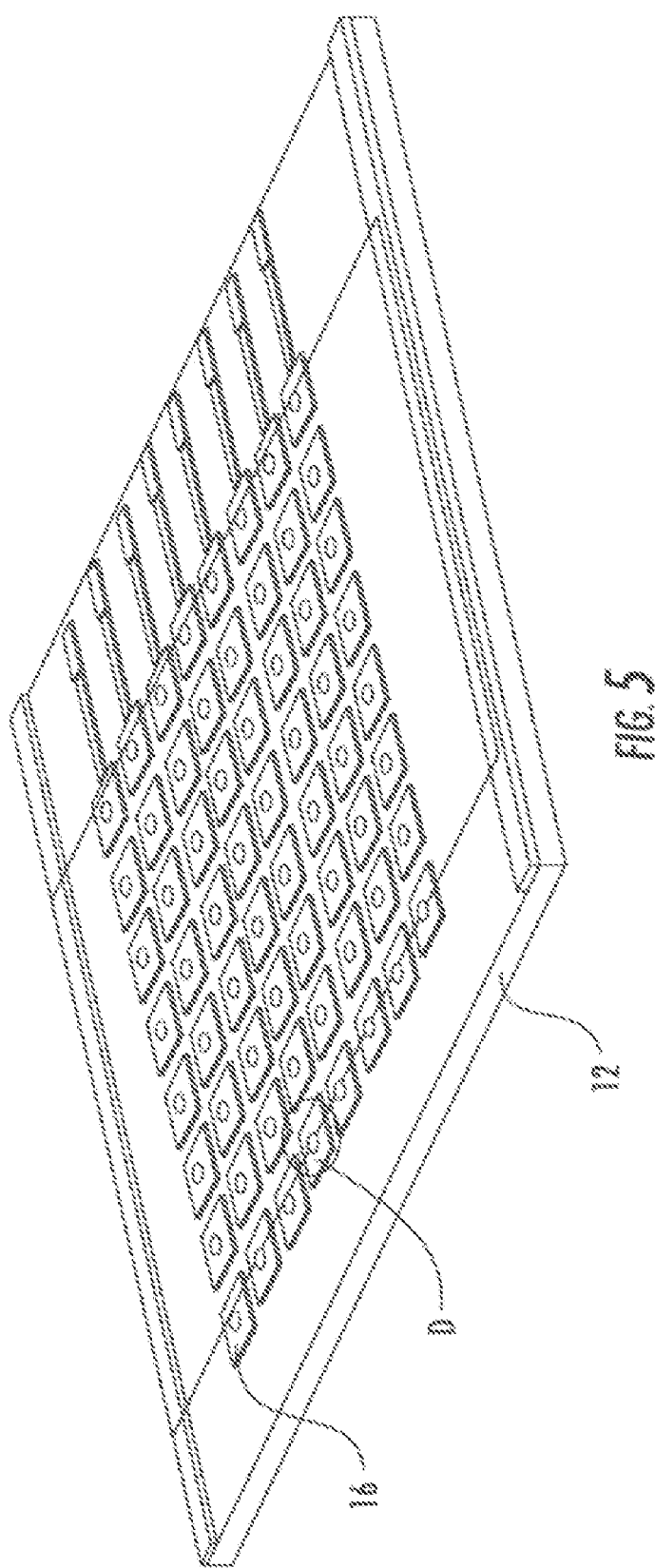

METHODS FOR NUCLEIC ACID AMPLIFICATION ON A PRINTED CIRCUIT BOARD

CROSS-REFERENCE TO RELATED APPLICATIONS

This application is a continuation of co-pending U.S. patent application Ser. No. 11/343,284; the disclosure of which is incorporated herein by reference in its entirety.

BACKGROUND OF THE INVENTION

1. Technical Field

The presently disclosed subject matter relates generally to nucleic acid amplification. More particularly, the presently disclosed subject matter relates to amplifying DNA or RNA on a printed circuit board (PCB) substrate.

2. Background

Microfluidics is a rapidly advancing field which deals with the study of sub-microliter fluids. Microfluidic devices are increasingly finding application and acceptance in many fields of biology, chemistry, medicine, environmental monitoring, drug discovery, and consumer electronics. Miniaturization of traditional devices, particularly analytical devices, is expected to lead to many benefits including reduced consumption (and cost) of reagents and samples, higher throughput and automation, faster analysis times, and more reliable, inexpensive, and portable instrumentation. As more functionality becomes embedded within these devices, fully integrated micro-total-analysis systems (μTAS) or labs-on-a-chip are becoming a reality and increasingly important.

Lab-on-a-chip is an emerging paradigm which aims to miniaturize and integrate fluid-handling onto a chip. A lab-on-a-chip should enable fluid dispensing, transport, mixing, incubation, detection/separation, and waste disposal for it to be a truly self-contained unit. Microfluidic lab-on-a-chip systems can be broadly categorized into continuous-flow and discrete-flow systems. A continuous-flow system is self-descriptive and in discrete-flow systems the fluid is discretized into droplets. A common limitation of continuous flow systems is that fluid transport is physically confined to fixed channels, whereas droplet-based (or discrete-flow) systems can be either confined to physical channels or operate on planar and channel-less systems. The transport mechanisms generally used in continuous-flow systems are pressure-driven by external pumps or electrokinetically-driven by high-voltages. Continuous-flow systems can involve complex channeling and require large supporting instruments in the form of external valves or power supplies. In another approach to channel-based systems, centrifugal forces drive the fluids to flow uni-directionally in channels. The continuous-flow microfluidics paradigm has limitations in versatility, making it difficult to achieve high degrees of functional integration and control.

Discrete-flow or droplet-based microfluidic systems have been progressing steadily to fulfill the promise of the lab-on-a-chip concept to handle all steps of analysis, including sampling, sample preparation, sample-processing including transport, mixing, and incubation, detection, and waste handling. These steps have been designed to be performed on-chip without significant off-chip support systems. A few discrete-flow approaches have been recently developed for manipulating droplets based on multilayer soft lithography, hydrodynamic multiphase flows, continuous electrowetting, electrowetting-on-dielectric (EWOD), dielectrophoresis, electrostatics, and surface acoustic waves. Some of the above techniques manipulate droplets or slugs in physically confined channels while other techniques allow manipulation of droplets on planar surfaces without any physically defined channels. The channel-less droplet-based approaches have been referred to as "digital microfluidics" because the liquid is discretized and programmably manipulated.

Droplet-based protocols are very similar to bench-scale biochemical protocols which are also generally executed on discrete volumes of fluids. Therefore, established protocols can be easily adapted to digital microfluidic format. Some of the distinguishing features of digital microfluidic systems include: reconfigurability (droplet operations and pathways are selected through a software control panel to enable users to create any combination of microfluidic operations on-the-fly); software programmability also results in design flexibility where one generic microfluidic processor chip can be designed and reprogrammed for different applications; conditional execution steps can be implemented as each microfluidic operation can be performed under direct computer control to permit maximum operational flexibility; multidirectional droplet transport since the channels only exist in the virtual sense and can be instantly reconfigured through software; small droplet volumes (<1 μL); completely electronic operation without using external pumps or valves; simultaneous and independent control of many droplets; and channel-less operation (where no priming is required).

Many current lab-on-a-chip technologies (including both continuous-flow and discrete-flow devices) are relatively inflexible and designed to perform only a single assay or a small set of very similar assays. Due to the fixed layouts of current microfluidic chips, a new chip design is required for each application, making it expensive to develop new applications. Furthermore, many of these devices are fabricated using expensive microfabrication techniques derived from semiconductor integrated circuit manufacturing. As a result, applications for microfluidic devices are expanding relatively slowly due to the cost and effort required to develop new devices for each specific application. Although batch fabrication allows microfabricated devices to be inexpensive when mass-produced, the development of new devices can be prohibitively expensive and time consuming due to high prototyping costs and long turn-around time associated with standard semiconductor microfabrication techniques. In order to broaden the range of applications and impact of microfluidics in medicine, drug discovery, environmental and food monitoring, and other areas including consumer electronics, there is a long-felt need both for microfluidic approaches which provide more reconfigurable, flexible, integrated devices, as well as techniques for more inexpensively and rapidly developing and manufacturing these chips.

Over the past several years there have been advances utilizing different approaches to microfluidics based upon manipulation of individual nanoliter-sized droplets through direct electrical control. Examples of such systems can be found in U.S. Pat. No. 6,911,132 and U.S. Patent Application Publication No. 2004/0058450, both to Pamula et al. (and commonly assigned to the Assignee of the present subject matter), the disclosures of which are incorporated herein by reference. These techniques offer many advantages in the implementation of the digital microfluidics paradigm as described above but current fabrication techniques to produce these microfluidic chips still depend on rather complex and expensive manufacturing techniques. These microfluidic chips are currently produced in microfabrication foundries utilizing expensive processing steps based on semiconductor processing techniques routinely used in the integrated circuit (IC) fabrication industry. In addition to higher cost for semiconductor manufacturing techniques, semiconductor foundries are not easily accessible and typically do not offer fabrication or prototyping turn-around times of as quick as 24 hours.

Microfluidic chips are generally fabricated using custom processes based on traditional semiconductor microfabrication procedures. Devices are fabricated on glass substrates through repeated steps of thin film deposition and patterning using standard photolithographic techniques. Typically, at least two metal layers (one for electrodes and one for wiring) are required in addition to two or three insulator layers, as well as layers for forming the standoff between the top and bottom plates. Due to the high cost of photomask fabrication and chip manufacturing, a single prototyping run producing up to 100 devices can cost as much as $10,000 and require three months to complete depending on the number of photolithographic levels. Furthermore, since the process flow is not standardized, device yields tend to be very low during the first several attempts to fabricate any new design.

The expense and time required for prototyping has been a serious impediment to the development and optimization of droplet-based microfluidics. Furthermore, the high chip costs and inability to rapidly customize or improve device designs is expected to dampen the commercial prospects of this versatile technology. In the short term, a more rapid, reliable and low cost fabrication technology is required to accelerate development and user acceptance of these devices. Since microfluidic structures tend to be relatively large and rarely test the limits of semiconductor manufacturing techniques, lower resolution, lower cost batch fabrication methods should be considered.

In particular, printed circuit board (PCB) technology offers many capabilities and materials similar to traditional semiconductor microfabrication though at much lower resolution. Layers of conductors and insulators are deposited and photolithographically patterned and stacked together to create intricate multi-level structures. For the fabrication of digital microfluidic systems, it is believed that PCB technology offers an excellent compromise in terms of resolution, availability, cost and ease of manufacture. It is further believed that an additional advantage of using a PCB as a substrate is that electronics for sensing, controlling or analyzing the device can be easily integrated at very low cost.

Typically, the copper line width and line spacing is measured in mils (25.4 µm) in a PCB process, which is orders of magnitude higher than the sub-micron features generally achieved in a semiconductor fab. Typically, PCB processing does not require an expensive ultra-clean environment as is required for semiconductor IC fabrication. The boards are also generally made out of reinforced plastic, glass fiber epoxy, TEFLON®, polyimide, etc. as compared to silicon or glass which are used as substrates for microfluidic devices microfabricated in a semiconductor fab. Also, in place of a semiconductor mask aligner, alignment can usually be performed manually for PCB processing. Inexpensive masks made out of transparencies or MYLAR sheets are used in place of expensive chrome-on glass photomasks used in semiconductor fabs. In PCB processing, via holes are drilled either mechanically or with a laser and then electroplated instead of etching and vapor deposition used in semiconductor processing which necessitates vacuum processing. Multiple wiring layers are generally obtained by bonding individually patterned single boards together as opposed to using a single substrate and building up the multiple layers or bonding wafers in a semiconductor fab. Broadly, these are the main differences between a PCB fabrication process and a semiconductor fabrication process even though high-end PCB processes are moving towards adopting some of the semiconductor processes (such as physical vapor deposition).

In today's highly competitive commercial environment, it is imperative that products reach the marketplace quickly and cost-effectively, particularly in consumer electronics and medical diagnostics businesses. The present subject matter is related to utilizing printed circuit board (PCB) manufacturing techniques which are widely available, reliable, inexpensive and well-defined. By fabricating reconfigurable microfluidic platforms with a reliable, easily accessible, and low-cost manufacturing technology, the development and acceptance of lab-on-a-chip devices for many potential applications in biomedicine and in other areas will be more widespread and rapid.

The attractiveness of PCB technology as an inexpensive, well-established, flexible and easily accessible manufacturing process for the development of microfluidic systems has already been recognized by researchers working with more traditional continuous-flow microfluidic systems. For example, researchers have previously demonstrated a number of continuous-flow microfluidic devices based on PCB technology including a bubble detector, a pH regulation system, a micropump, and a capacitive pressure sensor. More recently, PCB devices for the manipulation and analysis of single cells by dielectrophoresis have also been reported, as have hybrid approaches in which a PCB is used to monolithically integrate silicon-based microfluidic devices. However, there remains a long-felt need for an inexpensive, flexible, and reconfigurable system for discrete-flow manipulation of droplets.

BRIEF SUMMARY OF THE INVENTION

The methods as disclosed herein comprise a novel way of utilizing a substrate fabricated in a standard printed circuit board (PCB) process for amplifying nucleic acid through the use of digital microfluidic droplet manipulation. This unconventional use of established PCB processes incorporates various novel aspects including: (1) the use of copper traces and pads on a PCB as electrodes for droplet manipulation wherein fluids in the form of droplets are routed (i.e., transported) on the outer surfaces of a PCB substrate by electrical means (as opposed to placing electronic components and routing electronic signals); (2) the use of soldermask material as an electrode dielectric to act as an insulator for the electric-field induced droplet manipulation (as opposed to using the soldermask, as its name implies, to protect the copper wires from solder); (3) the use of photoimageable liquid or dry soldermask to make physical structures to hold fluids; (4) the use of via holes in the PCB for electrically connecting droplet control electrodes to each other or to contact pads; (5) the use of soldermask-filled via holes interior to the electrodes in the PCB to permit close packing of droplet control electrodes; (6) the filling of via holes interior to the electrodes with conductive epoxies to permit close packing of electrodes without loss of conductive area of the electrodes; (7) the filling of via holes interior to the electrodes with optically transparent epoxies for through-the-droplet optical measurements; (8) the use of copper traces adjacent to the electrodes, on the same surface of the PCB to provide a common reference potential (coplanar arrangement); (9) the use of copper embedded within the control electrodes and on top of the dielectric layer to serve as reference electrodes; (10) the use of drill-holes on the PCB for fluidic interfacing to permit input and output of fluids onto/off of the PCB; and (11) the use of copper lines as heating elements.

Methods for amplifying nucleic acid, such as DNA or RNA, on a printed circuit board (PCB) substrate are disclosed. The amplification can be achieved through a variety of methods such as thermocycling or isothermally. The printed circuit board substrate can comprise an array of electrodes for transporting droplets and can include a sandwich structure including a top plate parallel to the printed circuit board substrate.

It is therefore an object of the present subject matter to provide methods for amplifying nucleic acid through operating droplet-based microfluidic systems based on conventional printed circuit board (PCB) technology wherein droplets are actuated upon the PCB surface by application of electrical potentials to electrodes defined on the PCB.

An object of the presently disclosed subject matter having been stated hereinabove, and which is addressed in whole or in part by the presently disclosed subject matter, other objects will become evident as the description proceeds when taken in connection with the accompanying drawings as best described hereinbelow.

BRIEF DESCRIPTION OF THE DRAWINGS

FIG. 1A is a top plan and FIGS. 1B-1D are profile views of an embodiment of the present subject matter depicting a strictly co-planar arrangement on a PCB with filled or unfilled via holes within the electrodes;

FIG. 2A is a top plan and FIG. 2B is a profile view of an embodiment of the present subject matter depicting a substantially co-planar arrangement on a PCB with filled or unfilled via holes within the electrodes;

FIG. 3A is a top plan and FIG. 3B is a profile view of an embodiment of the present subject matter depicting an embedded co-planar arrangement on a PCB with filled or unfilled via holes within the electrodes;

FIG. 4A is a top plan and FIG. 4B is a profile view of an embodiment of the present subject matter depicting a parallel-plate or bi-planar arrangement on a PCB with filled or unfilled via holes within the electrodes;

FIG. 5 is a perspective view of a droplet positioned on a dense array of electrodes with via holes on a PCB for droplet manipulation in accordance with the present subject matter (liquid reservoirs not shown);

DETAILED DESCRIPTION OF THE INVENTION

Figure 6:
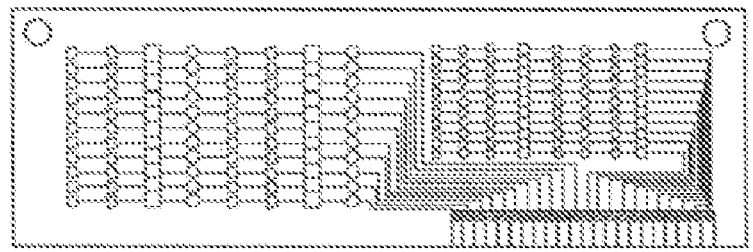
FIG. 6 is a photograph depicting the front side of a PCB chip used to test droplet transport performance of different shapes and sizes of drive electrodes in accordance with the present subject matter.
Figure 7:
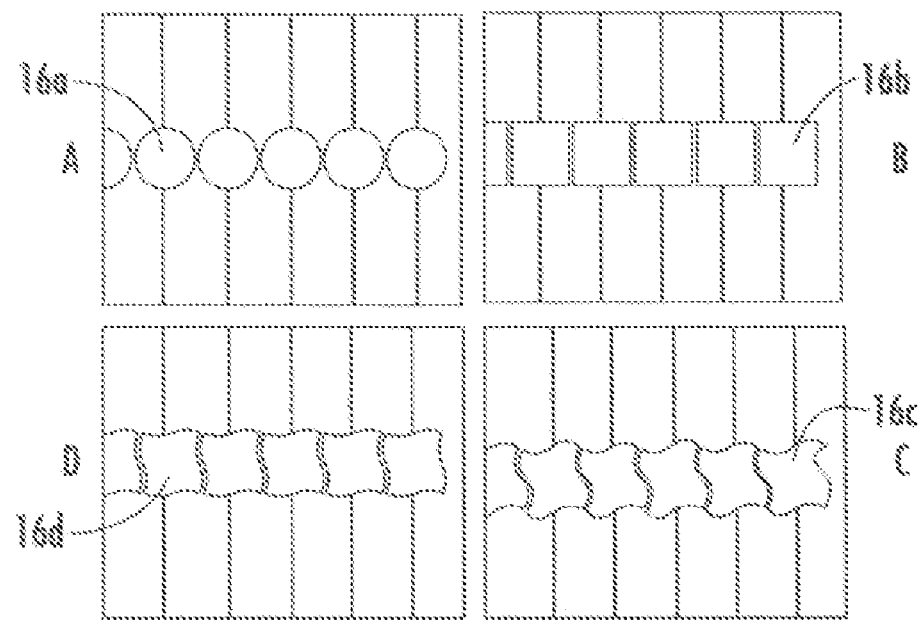
FIGS. 7A-7D are photographs depicting various electrode shapes in accordance with the present subject matter.

A printed circuit board (PCB), also sometimes called a printed wiring board (PWB), is a substrate used to interconnect electronic components using conductive pads and traces patterned on the substrate. Typically, PCBs are made by adhering a layer of copper over the entire substrate, sometimes on both sides, (known as creating a "blank PCB") then removing unwanted copper (e.g., by etching in an acid) after applying a temporary mask, leaving only the desired copper traces. Electrical connections ("vias") between opposite sides of the substrate can be formed by drilling holes through the substrate either mechanically or with a laser and metallizing the interior of the drill hole to provide a continuous electrical connection between the two sides. Multilayer boards can be created by bonding together individually processed substrates. Electrode lines in the copper layer are usually defined by etching copper from a blank PCB in a subtractive process while some foundries use semi-additive and fully-additive processes where copper is built up on the substrate by electroplating or other techniques.

As discussed above, digital microfluidics is a microfluidic approach in which discrete droplets of fluid are electrically manipulated upon a substrate containing an array on electrodes. In a commonly used configuration, the droplets are sandwiched between two parallel plates where the top plate physically confines the droplets and the bottom plate contains an array of individually addressable drive or control electrodes (or elements) which are electrically insulated. Typically, one or more reference electrodes (or elements) are also required to control the electrical potential of the droplet. Reference electrodes may be either provided on the same substrate as the drive electrodes (co-planar) or on an opposite plate (bi-planar). The space between the two plates surrounding the droplet is generally open and may be filled with air or with an immiscible liquid to prevent evaporation. Examples of immiscible liquids that may be used with aqueous droplets include silicone oil, fluorosilicone oil or hydrocarbon oils. When the reference electrodes and drive electrodes are provided on the same substrate, the opposing plate does not serve as part of the electrical circuit, but serves only as a cover plate to physically contain the liquids and may not be required for operation of the device.

Droplet actuation is achieved by applying a potential between the reference electrode and one or more of the drive electrodes. The applied potential can be DC or AC and the reference electrodes need not be physically distinct from the drive electrodes. A droplet adjacent to an activated control electrode will become attracted towards that control electrode and move towards it. Control electrodes may be sequentially activated using user-defined patterns (possibly using an electrode selector) to transport droplets along arbitrary pathways defined by contiguous control electrodes. In addition to transport, other operations including merging, splitting, mixing, deforming and dispensing of droplets can be accomplished based on the design of the control electrodes and patterns of activation.

A digital microfluidic processor is essentially comprised of an array of control electrodes with one or more reference electrodes. A complete chip may include many other types of structures including channels, liquid reservoirs, top-plates, sensors, inlets, outlets, etc. The electrode array requires interconnections to electrically connect certain electrodes together and to connect electrodes to contact pads for connection to external circuitry. Previously, digital microfluidic chips were fabricated on glass or silicon substrates using thin-film deposition and photolithography techniques borrowed from semiconductor manufacturing. Multiple levels of electrical interconnect for wiring were built-up by depositing and patterning successive layers of conductors and insulators upon a single starting substrate. The present subject matter pertains to apparatuses and methods whereby digital microfluidic processors can be advantageously constructed in a standard PCB process as opposed to a custom glass or silicon based process.

The presently disclosed subject matter takes advantage of the ease with which multiple layers of conductors can be generated in a PCB process versus a glass or silicon based process. This is essentially the case because in PCB processing the metal layers are manufactured on separate substrates which are laminated together at the end rather than built up sequentially on a single substrate.

The PCB digital microfluidic chip as envisioned herein can have one or more wiring layers. The conductor wiring patterns are transferred onto the PCB substrate by subtractive plating, panel plating, pattern plating, or additive plating. When only one layer of wiring is used, all the electrodes for droplet manipulation and the pads for electrical input/output connections are made on a single-sided board which does not require any via holes. Generally, two or more wiring layers will be required for complex droplet handling operations which necessitate using multilayer boards. Multilayer boards are assembled by bonding several double-sided boards or by built-up/sequential boards which do not require mechanical drilling of holes (e.g., via holes are chemically etched or laser drilled and then electroless plated). By definition, double-sided boards have wiring on both sides of the boards which can be further classified into boards without through-hole metallization and boards with through-hole metallization. The boards with through-hole metallization are further classified into plated through-hole metallization and filled through-hole metallization. In plated through-hole metallization, the holes are metallized by copper plating (e.g., electroplating or electroless plating or a combination thereof) and in filled through-hole metallization, the holes can be filled with conductive pastes such as copper paste, silver paste, conductive epoxy, etc.

In digital microfluidic chips, through-holes (or via holes) are drilled through the center of the drive electrodes on one side of a multi-layer board to make electrical connections on the opposite side of the board. The foot print of a droplet is defined by the area of a drive electrode. In order to obtain small droplet volumes, the area of the drive electrodes need to be minimized. Since via holes are drilled through the drive electrodes, it is important to minimize the diameter of the via holes including the pad/land diameter. Therefore, via holes play an important role in defining the minimum volumes of droplets obtainable in a PCB process. The PCB industry is driving down the via hole sizes for a different reason which is to avoid blocking the wire routing channels and to maximize the PCB surface area available for traces. Many built-up processes use small vias which are formed by punching through using an excimer laser. There are a number of variations of the built-up processes used in the PCB industry including, but not limited to, Surface Laminar Circuits (SLC) where the vias are photoformed; DYCOstrate™ where the vias are dry-plasma etched in parallel; Film Redistribution Layer (FRL) where the outermost dielectric is photosensitive while inner layers constitute a regular multilayer board; Conductive Adhesive Bonded Flex (Z-Link); Built-up Structure System (IBSS) where the dielectric is photosensitive; Sequential Bonding Cores/Any-Layer Inner Via-hole (ALIVH) where a $CO_2$ laser is used to drill the vias and the holes are then filled with silver paste; Carrier Formed Circuits where separate circuits are prepared on stainless steel carriers and then laminated onto an FR-4 prepreg; Roll Sheet Buildup where single-sided epoxy coated foils are laminated by rolling heat and pressure; and Sheet Buildup which is similar to roll sheet buildup but double sided or multilayer circuits are laminated. In one embodiment of using a built-up board (Z-Link) for digital microfluidic chips, multiple flex boards consisting of polyimide-backed copper foils can be laminated together and then onto a rigid board to form a multi-layer board. In this case, the holes in each flex layer can be punched, laser-drilled or plasma-drilled. The holes interconnecting various layers can then be filled by conductive adhesive.

General Embodiments

With reference to FIGS. 1A-1D, 2A-2B, 3A-3B, 4A-4B, and 5, the requirements for adapting PCB processed substrates for droplet manipulation will now be discussed in more detail. As will be discussed in further detail below, FIGS. 1A-1D relate to a PCB digital microfluidic chip 10 including a strictly co-planar arrangement on a PCB with filled or unfilled via holes within the electrodes; FIGS. 2A-2B relate to a PCB digital microfluidic chip 20 including a substantially co-planar arrangement on a PCB with filled or unfilled via holes within the electrodes; FIGS. 3A-3B relate to a PCB digital microfluidic chip 30 including an embedded co-planar arrangement on a PCB with filled or unfilled via holes within the electrodes; FIGS. 4A-4B relate to a PCB digital microfluidic chip 40 including a parallel-plate or a bi-planar arrangement on a PCB with filled or unfilled via holes within the electrodes; and FIG. 5 depicts a droplet positioned on a dense array of electrodes with via holes on a PCB for droplet manipulation. FIG. 5 generally shows the concept of the present subject matter wherein liquid samples are digitized into discrete droplet(s) D which can then be independently dispensed, transported, incubated, detected or reacted with other droplets (the approach of "digital microfluidics").

In each of the embodiments shown in FIGS. 1A-1D, 2A-2B, 3A-3B, and 4A-4B, and as will be described individually in more detail below, a PCB substrate board 12 is provided, the board having a top first side surface 13 and a bottom second side surface 14. Drive control electrodes (or elements) 16, such as copper trace drive electrodes, can be provided on top surface 13 of PCB 12, and reference electrodes (or elements) 18, such as copper trace reference electrodes or a parallel plate reference electrode, can also be provided in a variety of configurations for droplet manipulation. Soldermask, such as liquid photoimageable (LPI) soldermask, is typically used in traditional PCB processes as the outer layer to protect copper lines from the action of etchants or plating or from solder during the placement of electronic components. However, in its utility for driving droplets according to the present subject matter, this outer layer is an insulator 22 that serves to insulate the droplets from the potentials applied on drive and reference electrodes 16, 18. Drive electrodes 16 are completely insulated by insulator 22, preferably a LPI soldermask or some other dielectric including temporary soldermasks. Complete insulation means that drive electrode 16 is covered on all sides including the edges. Insulator 22 (LPI soldermask) is applied using conventional processes which include, but are not limited to, curtain coating, spin coating, spray coating, or screen printing. In case there is a need for a reference electrode 18, some of the copper features can be left bare and not insulated to provide a direct reference potential to the droplets. This exposed portion is as close to drive electrodes 16 as permitted by the PCB process which is defined by the resolution of the copper features as well as the resolution of the soldermask and the registration of the soldermask layer to the copper layer. The exposed portion of reference electrode 18 may have an optional conductive surface finish which commonly includes immersion silver, immersion gold, and electroless nickel/immersion gold (ENIG).

Substrate Material

As discussed above, electrostatic microfluidic devices of the present subject matter include a substrate board 12 which can be fabricated on almost any board material commonly in use for the manufacture of PCBs. These materials include, but are not limited to, FR-2, FR-4, FR-5, polyimide, Kapton™, Rogers™, Duroid™, BT, cyanate esters and Polytetrafluoroethylene (PTFE). Rigid, rigid-flexible or flexible substrates can be used as base material 12 for the fabrication of these devices.

Electrode Formation

The outermost conductive copper layer of the PCB is patterned to form the drive electrodes required to manipulate liquid droplets by electric fields. Drive electrodes 16 may take a wide variety of shapes and forms depending on the particular application. For example, arrays of square-shaped electrodes, arrays of circular-shaped electrodes, arrays of hexagon-shaped electrodes, arrays of star-shaped and other interlocking or interdigitated electrode shapes, as well as elongated electrode structures can be used. Reference electrodes 18 can also be patterned in the same conductive layer or in a separate conductive layer on the same substrate (coplanar) or can be provided on a separate substrate (bi-planar).

In one embodiment as shown in FIGS. 1A-1D, reference electrodes 18 can be patterned in the same conductive copper layer as drive control electrodes 16 wherein insulator 22 is removed over portions of reference electrodes 18 to expose the conductive layer underneath. This pattern permits simultaneous electrical contact between reference electrodes 18 and the liquid droplet. In this embodiment, reference electrodes 18 may be located adjacent to or in between drive control electrodes 16.

In another embodiment as shown in FIGS. 2A-2B, reference elements 18 can be formed as a separate conductive layer patterned directly on top of insulator 22. The conductive layer may be a thin metal film deposited by vacuum processing, electroless plating, electroplating, lamination or other means and patterned to form reference elements 18. Reference elements 18 may take a variety of shapes and forms and may lie either directly above and/or to the side of drive elements 16 (i.e., reference elements 18 need not be precisely aligned to drive control elements 16). In one arrangement, reference elements 18 may form a grid or mesh of conductive lines superimposed over drive elements 16. In this arrangement, reference elements 18 could electrically shield control electrodes 16 where they overlap, so the overlap should ideally be minimized when sizing and locating reference elements 18 relative to drive control elements 16.

In another arrangement, the pitch of the grid is chosen to be less than, but not an integer factor of, the electrode pitch. This separate conductive layer arrangement may be realized using additive metal PCB processes where metal is deposited upon insulator 22 or alternatively could be realized using subtractive processes where reference elements 18 and drive elements 16 are formed on opposite sides of a thin flexible circuit substrate. In the latter case, the flexible circuit substrate serves as the insulation for drive control elements 16 and the flexible circuit can be laminated to a rigid substrate to provide mechanical rigidity and to provide electrical interconnections for the electrodes.

In a further embodiment as shown in FIGS. 3A-3B, reference elements 18 can be provided in an embedded co-planar arrangement within drive control elements 16. In such an arrangement, via holes 25 with plating 26 can function as reference elements 18 in areas not covered by insulator 22. Other via holes 24 with plating 26 covered by insulator 22 can also be provided and function as described hereinbelow.

In another embodiment as shown in FIGS. 4A-4B, reference elements 18 can be provided on a separate substrate as a parallel plate. Typically, the substrate containing drive electrodes 16 and the substrate containing reference elements 18 are placed in opposition to each other with a gap G between them to contain the liquid, thereby creating a sandwich structure. An additional parallel-plate arrangement can include two opposing surfaces that are electrostatic PCB microfluidic devices by themselves (the upper "plate" can be a PCB having a top first side surface 13' and a bottom second side surface 14') and have drive elements 16 on both surfaces and reference elements 18 on at least one surface.

Because very little current is needed to charge drive electrodes 16 for electric field-based droplet manipulation, the conductive material forming the electrodes can be substantially more resistive than is typically acceptable for PCB applications. Thus, a wide range of different types of conductors, besides copper, may be used. This includes conductors which are typically considered unsuitable for forming pads and traces on PCBs. Similarly, the conductive layer may be substantially thinner than is typically favored for PCBs. Ideally, the conductive layer should be as thin as possible to minimize the topography of the conductive features which must be subsequently covered by the insulating layer. Additionally, minimization of the conductor thickness promotes planarity of the PCB surface which is desirable for consistent and reliable manipulation of droplets upon the surface. The conductor thickness may be minimized by using a starting substrate material with minimal conductor thickness (e.g., ¼ oz. or 5 µm layer of copper cladding) or by adding a polishing or etching step to reduce the conductor thickness prior to deposition of the insulator.

Electrode Interconnection and Vias

Conductive traces on PCB substrate 12 are used to make electrical connections to drive electrodes 16 and reference elements 18. Each drive electrode 16 or reference element 18 can be connected to one or more other drive electrodes 16 or reference elements 18, to other electronic components on the same PCB substrate 12, or to pads for external connection. In one arrangement, pads for external connection are provided along an edge of the PCB and the PCB is adapted for use in an edge-card connector socket 28 (see FIGS. 8A-8B). In another arrangement, an array of pads is disposed on the surface of the PCB and the pads are contacted using spring-loaded pins, test clips or a strip of anisotropically conducting material 29 (see FIG. 9A). In yet another arrangement, a pin-header, socket connector or other discrete electronic component is connected to the PCB to facilitate connection to an external circuit.

As shown in FIGS. 1A-1D, 2A-2B, 3A-3B, and 4A-4B, electrical connections between different conductive layers of substrate 12 can be made through PCB methods as known in the art, whereby a hole or via hole 24 is drilled through substrate 12 from the two conductive regions (top surface 13 and bottom surface 14) on either side of substrate 12 and which are to be electrically connected. While shown as circles in the drawings, it is understood that via holes 24 can be any shape such as squares, ovals, etc. that could be formed in substrate material 12. The interior of hole 24 can also be metallized by electroless plating or electroplating or using other methods to form a plating 26 (plated-through hole metallization) so that electrical continuity is established between the two opposite sides at the location of the via hole. As discussed above, conductive pastes (filled through-hole metallization) could also be used in lieu of plated through-hole metallization to establish electrical continuity.

In order to establish electrical connections between electrodes and traces several approaches are available. In one approach, a wire or trace leads away from the electrode on the same side of the PCB, the wire can then be routed if necessary through the substrate at a via location remote from the electrode. In another approach, vias are made within the electrodes. In this case a means for filling or covering the drill hole may need to be provided to prevent liquid from entering or evaporating through the via drill hole. Via hole 24 may be plated shut using electroless or electroplating or may be filled or covered using a variety of techniques and a variety of materials (conductive epoxy, non-conductive epoxy, transparent epoxy, or any other material). After filling the via holes with any of these filler materials, the surface of the PCB can then be covered with copper by electroless or electroplating to completely obscure the via hole to the droplets moving on the surface.

In one approach, the hole is made small enough so that an insulator deposited in liquid form, such as a traditional liquid soldermask material, is prevented from penetrating the hole by viscous or surface tension effects, or it could be made large enough so that the liquid soldermask can enter the via hole thereby forming a soldermask-filled via hole 24' (see FIG. 1B). Alternatively, an extra process step may be added to fill the drill holes with an epoxy or similar material prior to depositing the insulator, thereby forming an epoxy-filled via hole 24" (see FIG. 1C), or a transparent epoxy-filled via hole 24'" (see FIG. 1D). Another approach is to use a dry film insulator material which "tents" the drill hole, effectively covering it and sealing the chip surface. A possible disadvantage of several of these approaches is that they result in the formation of a non-conductive region within the border of the otherwise conductive electrode which reduces the area of that electrode that can be used for electric field generation. In order to address this issue, several techniques are available for producing a conductive filling, including the use of conductive epoxies to fill the hole and the use of electroless plating or electroplating to provide a conductive surface coating over a non-conductive filler material. Another alternative is to electroplate the drill hole so that it becomes completely filled with metal. This approach may require a planarization step to remove the excess metal deposited on the substrate surface by the greater amount of electroplating. Planarization and control of the conductor thickness on the substrate surface can be simplified in this case through the use of a "button-plating" process in which additional metal is only added in the region surrounding the via. The resulting "buttons" can be then be removed by polishing the surface of the PCB. In this method, substantial amounts of metal can be deposited within the drill-holes without increasing the final thickness of the metal on the PCB surface.

Electrode Insulation

Referring further to FIGS. 1A-1D, 2A-2B, 3A-3B, and 4A-4B, drive electrodes 16 are typically electrically insulated by insulator 22 to prevent the flow of direct electric current between the electrodes and the conducting liquid when a DC potential is applied to the drive electrodes. It should be noted that AC potentials could as well be applied to the drive electrodes to enable electric-field induced droplet manipulation. While any dielectric can be used, soldermask is typically used in traditional PCB processes to protect the copper lines on a PCB and to expose copper only where electronic components will be eventually soldered. The most straightforward approach for insulating drive electrodes 16 is to use soldermask material (or other dielectric) as electrical insulator 22. Both liquid and dry-film soldermasks are suitable for use as electrode insulators 22. Photoimageable soldermasks are generally preferred because they can be readily patterned to provide electrical access to reference elements 18 or contact pads underneath insulator 22.

Soldermasks are available in two varieties: liquid photo-imageable (LPI) or dry film soldermask (DFSS). LPI is not conformal. DFSS offers near vertical sidewalls and has been reported for fabricating electroplating molds, sealing of fluidic channels and as a mask for powderblasting of microchannels. However, DFSS has not been used to form liquid reservoirs or as a gasket material to provide a stand-off or seal between two parallel plates as is envisioned in the present subject matter.

In certain applications, soldermask materials may not exist with the desired combination of thermal, mechanical, electrical or optical properties. In these cases, the soldermask materials can be replaced with or combined with other types of insulator materials. For example, spin-on materials such as polyimide, dip or spin or spray or brush-coatable materials such as TEFLON® AF and Cytop™, vapor deposited or sputtered materials such as silicon dioxide, and polymers such as parylene may be applied to the PCB substrate.

As an alternative to soldermask for insulator 22, a thin layer of parylene could be deposited in a physical vapor deposition (PVD) process as a dielectric. Parylene is the generic name for a family of poly(para-xylylene) polymers which includes parylene C, D, and N. As used in this disclosure, parylene refers to any poly(para-xylylene) composition and mixtures thereof. A major advantage with parylene is that it can be deposited as a conformal layer and at a thickness much less than both LPI and DFSS. In PCB methods, LPI can be coated as thin as 0.5 mils (1 mil=25.4 µm) while pin-hole free parylene can be coated as thin as 0.5 µm. Such a thin insulator layer reduces the required potential for droplet actuation. In some applications, the dielectric will have to be patterned to expose the copper electrodes. Parylene can be patterned by reactive ion etching, plasma ashing, chemical etching, or by laser ablation. Alternatively, parylene can also be selectively deposited by masking the regions that need to be exposed by a tape (for example, 3M® Mask Plus II Water Soluble Wave Solder Tape No. 5414 which is used to mask gold fingers on PCBs during wave soldering). Other representative examples of materials that could be used as dielectrics include silicones, polyurethanes, acrylics, and other spin-coatable or depositable dielectrics.

Generally, it is desirable to minimize the thickness of insulator 22 in order to reduce the voltage required for actuation of the liquid.

Standoff Layers

It is also envisioned that additional layers of soldermask material may be deposited and patterned to create physical structures on the PCB surface such as wells and channels (not shown) for use in pooling or directing liquid flow.

Additional Processes

Combination of Subtractive and Additive Processing

In a further embodiment, a combination of subtractive and additive processes can be used to fabricate PCB droplet manipulation boards of the present subject matter. Subtractive processes can be used to fabricate a multilayer board that defines all the electrical routing and interconnections to the droplet control electrodes. A patternable dielectric layer can then be applied. Vias can be patterned in this dielectric by laser drilling or photomasking. In one embodiment, LPI can be used as a dielectric. The electrode pad exposed in the hole can be optionally plated to make it planar with the dielectric surface. At this point, an additive process can be used to define all electrodes using electroless copper deposition as a smaller line spacing could be obtained.

Post Processing

A finished device can include a combination of standard PCB processes and non-standard processes. For example, a one-step hydrophobic coating may be applied to a finished PCB to facilitate transport of droplets. Furthermore, the use of soldermask as a dielectric might be undesirable for certain applications, in which case uninsulated PCBs could subsequently be coated with specialty materials not available in a standard PCB process. However, in such cases, the use of a PCB as the starting substrate and PCB processes to form the conductive traces still provides many, if not most, of the benefits of a fully PCB-compatible process.

In one embodiment, all the conductor lines required for electrical routing can be fabricated on a multi-layer PCB. Some or all of the outer layer of copper can then be removed by polishing or chemical etching. This PCB, which contains all the electrical wiring required for droplet manipulations, can then serve as a substrate for further processing to pattern drive and reference electrodes with finer line spacing. In order to obtain fine line spacing, the control electrodes may be patterned using semiconductor processing techniques including thin film deposition and photolithography.

Plating up of Coplanar Reference Elements

In an embodiment where reference electrodes 18 are also patterned in the same layer as drive electrodes 16 (see, for example, FIGS. 1A-1D), there can be a significant dimple in the LPI soldermask as it only covers the drive electrodes and leaves the reference electrodes open. This dimple could affect the reliability of operation as the droplet may not be in contact with the reference element. In this case, the reference electrodes can be plated up such that the surface of the reference element is planar with the LPI soldermask (not shown). This plating step could be performed prior to the surface finish with copper or nickel.

Reference Electrodes on Outer Surface

In one embodiment, after all the copper electrodes are formed as described hereinabove, the LPI coating can then be used as an inter-level dielectric and another copper layer can be patterned over the LPI to serve as reference electrodes. The dielectric can also be a thin (2 mil or less) prepreg PCB board in a typical multilayer construction or it could be a flex board with copper features to serve as reference electrodes on the outermost layer. The copper layer just beneath this outermost copper layer has copper features that define the drive electrodes.

Integration of Electronics and Detection onto the PCB

In a further embodiment, it is envisioned that the PCB of the present subject matter may also consist of electronic components in the areas which are not used for liquid handling. The electronic components can include microcontrollers, relays, high voltage multiplexers, voltage converters (DC-DC to step up the voltage, DC-AC, AC-DC, etc.), electro-optical elements such as LEDs, photodiodes, photo-multiplier tubes (PMT), heating elements, thermistors, resistance temperature devices (RTDs), and other electrodes for electrochemical measurements. Copper traces can also be used for impedance measurements of the droplets. Resistive heating elements are realized by meandering copper traces and the resistive heating characteristics will be dependent on the dimensions of the copper lines. In one embodiment, a PCB containing an optical detector, such as a PMT or a photodiode, can be used as a parallel plate to form a sandwich with the droplet manipulation PCB board. In another embodiment, gold coated electrodes obtained in a standard PCB process can be used for electrochemical measurements.

Drill Holes for Fluidic Input/Output

Mechanically drilled holes on a PCB are used typically for affixing or securing the board to another surface. It is further envisioned in the PCB microfluidic chip of the present subject matter that these drill holes can be used to serve as fluidic input/output ports for the addition and removal of liquids to or from the surface of the PCB substrate. It is further envisioned that these drill holes can be mated with a source of liquid including, but not limited to, flexible tubing, syringes, pipettes, glass capillary tubes, intra-venous line, or microdialysis lumen. The liquid in these tubes can be driven by pressure or any other means. A continuous flow of liquid from the tubing can be interfaced to the PCB through these drill holes which can be discretized into droplets either directly from the flow or through an intermediate reservoir on the PCB.

For instance, in one embodiment, metallized drill holes (see, for example, drill holes 32 in FIGS. 9A-9B) can be located adjacent to control electrodes in order to serve as fluidic input/output ports for placing or removing liquids onto the electrode surface. In another embodiment, non-metallized drill holes (see, for example, drill holes 34 in FIGS. 9A-9B) can be provided for fluidic input and output and can be connected to a channel etched in solder mask which then leads to a reservoir (not shown). This reservoir can have electrodes for dispensing, such as by using electric-field mediated droplet dispensing techniques. In yet another embodiment, metallized drill holes provided for fluidic input/output can be covered by a dielectric and in addition have concentric rings of electrodes around the drill hole. In this case, droplets may be dispensed radially out of the hole by pressuring the liquid through the hole and then using an electric field to dispense droplets on the electrodes. In an additional embodiment, drill holes can be used to output liquid into a waste reservoir or any other container off-chip by collecting the droplets in the hole area and allowing the droplets to drip by gravity into a container placed underneath the hole.

Out of Plane Droplet Extraction from Via Holes

Generally, droplets moved on apparatuses of the present subject matter are manipulated within a horizontal plane in a sandwich structure with one or both of the plates comprising PCBs. In a further embodiment, the holes drilled on a PCB could be used to extract droplets out of the sandwich structure in a vertical plane. Droplets can be extracted through the holes in a variety of ways. In one method that exploits the pressure difference between a droplet confined in a sandwich structure and a large hole, droplets could be passively pushed through a hole with a diameter larger than the radius of the droplet by just positioning underneath the hole. Droplets could also be extracted by electrical means where another plate is added to the sandwich structure and the droplets can be pulled out of one sandwich structure into the newly-formed sandwich structure by applying an electric potential. In this case, to simplify the extraction process, a sandwich structure can be formed between a coplanar PCB substrate and another substrate with electrodes. While both these plates form a parallel-plate arrangement, the droplets will be touching only the coplanar PCB substrate and will move vertically onto the other substrate when an electric potential is applied on the other substrate to electrostatically pull the droplet out of plane. Droplet could also be moved vertically with gravity for stamping onto another plate. Applications for such vertical actuation of droplets include DNA or protein stamping applications. Droplets extracted from such holes can also be used to increase the path length for absorbance measurements and to transport into another sandwich structure to enable transport in another layer.

Biochemical Synthesis and Analysis

A number of biochemical reactions can be performed through the manipulation of liquids on PCB substrates as disclosed in the present subject matter. As disclosed herein, the present subject matter provides an apparatus for detecting a target analyte in sample solutions by optical and electrical means of detection. The sample solution may comprise any number of items, including, but not limited to, bodily fluids (including, but not limited to, blood, sweat, tears, urine, plasma, serum, lymph, saliva, anal and vaginal secretions, semen, of virtually any organism, with mammalian samples being preferred and human samples being particularly preferred); food and environmental samples (including, but not limited to, air, agricultural, water, and soil samples); biological warfare agent samples; research samples; purified samples, such as purified genomic DNA, RNA, proteins, cells, etc.; and raw samples (bacteria, virus, fungus, etc). The types of assays that can be performed on the PCB substrate as disclosed herein include enzymatic assays, DNA amplification isothermally or by thermocycling, immunoassays, including sandwich and homogeneous arrangements, and cell-based assays with optical and electrical means of detection. The analytes measured in the physiological samples includes metabolites, electrolytes, gases, proteins, hormones, cytokines, peptides, DNA, and RNA.

In one embodiment, a human physiological sample can be input into a reservoir on the PCB. The reservoir could be defined by the dry film soldermask. The sample can then be dispensed into droplets which will be mixed with the appropriate reagent droplets provided on the PCB or input onto the PCB. Some of the enzymatic assays can then be monitored optically (e.g., by absorbance, reflectometry, fluorescence, and luminescence). In the case of absorbance, the via holes can be filled with an optically transparent material so that the light can pass through a droplet positioned on one of these via holes for absorbance measurements.

In another embodiment, biochemical samples can also be synthesized on a PCB substrate using droplet manipulation techniques described herein. For example, on the PCB, a number of protein droplets can be dispensed from a reservoir and mixed with different reagents and incubated to automate finding conditions to crystallize a protein.

Sidewall Transport

In a further embodiment, copper traces with thickness on the same order as the droplet height can be used so that the droplet is contained between the traces lying on the same substrate and covered with an insulator. The droplet is actuated through electric fields applied primarily in the plane of the substrate rather than perpendicular to it. Unlike the coplanar arrangement, where the droplet sits on the coplanar drive and reference electrodes and parallel-plate arrangement, where the droplet is sandwiched between the drive electrodes on a substrate and a common reference electrode on a parallel substrate, in this structure a droplet is sandwiched between the coplanar drive and reference electrodes.

Specific Embodiment

While general embodiments and processes of the present subject matter have been discussed hereinabove, more specific embodiments of fabrication of an apparatus to manipulate micro-volume liquid samples wherein the apparatus comprises a printed circuit board substrate will now be discussed.

In a preferred embodiment, a FR-4 substrate is laminated with a ¼ Oz (~9 µm) copper foil on both sides. 8 mil via holes are drilled through the substrate. These via holes are then electroplated with copper and filled with soldermask or an epoxy. Preferably, the via holes are button-plated to a thickness of about 5 µm where the via holes are specifically plated while the rest of the board is covered by a mask. The buttons are mechanically planarized and then the via holes are filled with soldermask or a non-conductive epoxy. After processing the via holes, a flash plating step is performed to a thickness of less than 5 µm. In case unfilled via holes are required, another step of drilling can be performed to obtain unfilled holes and plating is performed if necessary. At this stage, the designed electrode pattern is transferred onto the copper with a minimum line spacing of 2 mils by etching it through a mask. LPI is patterned and coated to a thickness of about 0.5 mils. Finally, a dry film soldermask is laminated and patterned to form the physical structures (e.g., wells and/or channels) to hold liquids and also to serve as a stand off material. In other embodiments, the stand off layer can also be obtained by using one of more LPI soldermask coatings or by laminating and etching a copper foil.

Experimental Testing and Results

Experiments were conducted wherein a two-layer single-board design for an electric field-mediated droplet manipulator as disclosed herein was submitted to a commercially available electronics PCB manufacturer and tested. The design consisted of arrays of different control electrode shapes for transport and mixing of liquid droplets as well as specialized electrode shapes for dispensing of droplets from a larger liquid volume. The electrodes were connected to contact pads by conductive traces patterned in the same layer of copper on the surface of the PCB. Where necessary, the traces were routed between the two sides of the board using conventional vias at remote locations from the control electrodes. Several different chip designs and interconnection schemes were tested.

Some chips contained multiple copies of a single linear array of electrodes where the corresponding elements in each copy of the array were connected to the same electrical signal—thus multiple identical arrays could be controlled simultaneously. Other chips contained an electrode "bus" or conveyor structure where every fourth electrode in a contiguous line of control electrodes was connected to the same control signal. The use of such a structure allows arbitrarily long transport pathways to be controlled using a fixed number of control signals. Multiple droplets can be switched onto or off of the bus and synchronously transported. The contact pads were arranged along the side of the PCB and were designed to be contacted either using a standard edgecard connector or a standard SOIC test clip.

Figure 8A:
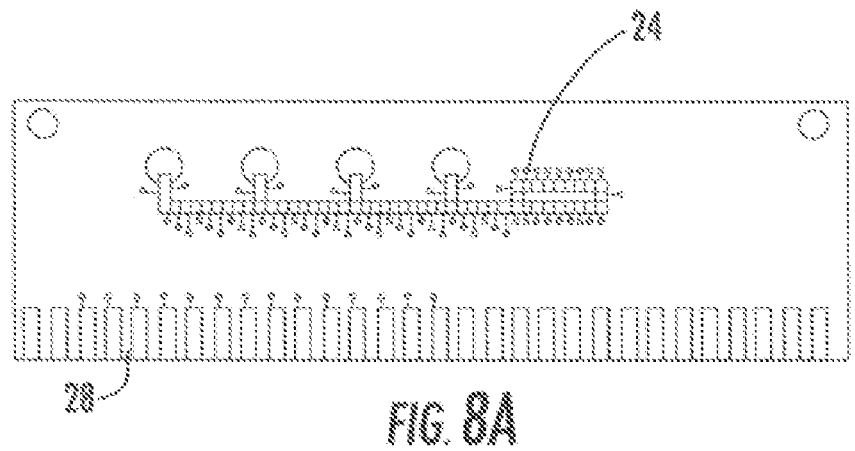
FIGS. 8A-8B are photographs of an embodiment of the present subject matter depicting front and back views, respectively, of a PCB chip design featuring a three-phase droplet conveyor and other structures for dispensing, storing and mixing droplets.
Figure 8B:
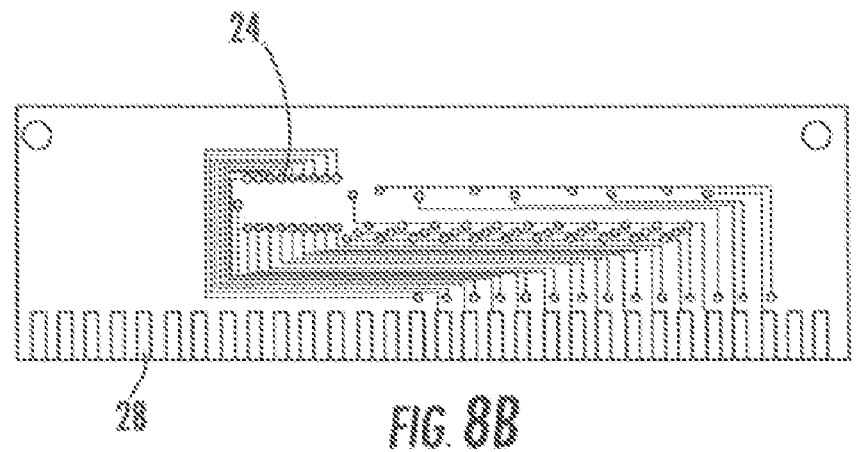
Figure 9A:
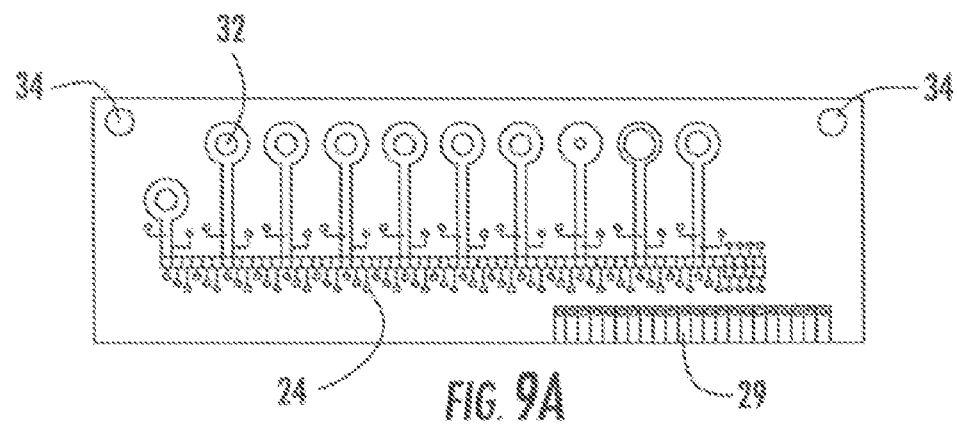
FIGS. 9A-9B are photographs of another embodiment of the present subject matter depicting front and back views, respectively of a PCB chip design featuring a three-phase droplet conveyor and other structures for dispensing, storing and mixing droplets.
Figure 9B:
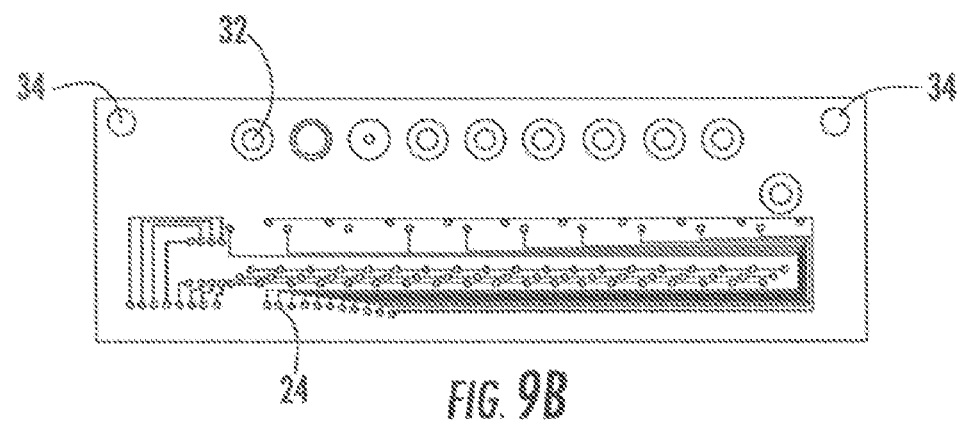

FIGS. 6, 7, 8A-8B, and 9A-9B illustrate several examples of chips manufactured for experimental purposes. FIG. 6 illustrates the front side of a PCB chip used to test droplet transport performance of different shapes (circular 16a, square 16b, star with small curvature 16c, star with larger curvature 16d) (see FIG. 7) and sizes of control electrodes (results discussed in reference to FIGS. 10-12 below). The chip illustrated in FIG. 6 contains 16 different linear electrode arrays. FIGS. 8A and 8B are front and back views of a chip design featuring a three-phase droplet conveyor as well as other structures for dispensing from an on-chip reservoir, storing and mixing droplets. Vias 24 are used to route the electrical signals from the backside of the PCB to the control electrodes on the front side and electrical contact is made through edgecard connector socket 28 located along one side of the PCB. FIGS. 9A and 9B are front and back views of another chip design featuring a three-phase droplet conveyor as well as other structures for dispensing from a fluidic input/output port 32, storing and mixing droplets. Vias 24 are used to route the electrical signals from the backside of the PCB to the control electrodes on the front side and electrical contact is made through an array of pads designed to be contacted using an SOIC test clip 29.

The arrays of control electrodes were designed with a pitch of either 1.0 mm or 1.5 mm and a nominal 2 mil spacing between adjacent electrodes. The substrate material was FR-4 with ¼ oz. copper cladding. The copper was patterned to form the control electrodes, traces and contact pads. The nominal minimum linewidth/spacing of the process used was 2 mil/2 mil, which was the spacing used between adjacent electrodes as well as the trace width between the control electrodes and contact pads. A liquid photoimageable soldermask material, CARAPACE® EMP 110 (available from Electra Polymers & Chemicals, Ltd.) was used as the electrode insulator. The nominal thickness of the soldermask insulator was 0.6 mil. After the PCBs were received from the manufacturer a thin hydrophobic coating of TEFLON® AF was applied to the top surface of the chip. TEFLON® AF was applied by spin-coating a 1% solution in FC-75 at 3000 rpm for 20 seconds onto the PCB surface, followed by a 30 minute cure at 150° C.

The PCBs were assembled as a sandwich with an indium-tin-oxide coated glass top-plate. The top-plate was also coated with a thin layer of TEFLON® AF so that all interior surfaces in contact with the droplet were hydrophobic. The conductive indium-tin-oxide film on the top-plate was used as the reference electrode. The PCB and top-plate were separated by a gap of approximately 0.8 mm. One or more droplets of electrolyte (0.1 M KCl) were injected into the sandwich structure and deposited on a control electrode. The volume of the droplet was sufficient to cover a single electrode and was approximately 2.2 µL for the 1.5 mm pitch electrodes and 1.1 µL for the 1 mm electrodes. The remaining volume between the two plates was filled either with air or with low viscosity (1 cSt.) silicone oil.

Referring to FIGS. 6, 7, and 10-12, tests on the transportation of droplets by sequential activation of the control electrodes as described in U.S. Pat. No. 6,911,132 and U.S. Patent Application Publication No. 2004/0058450, both to Pamula et al., were performed. Using a PCB similar to that shown in FIG. 6, tests were performed on 4 different electrode shapes (circular 16a, square 16b, star with small curvature 16c, star with larger curvature 16d) (see FIG. 7) in each of the two electrode sizes (1.0 mm and 1.5 mm pitch).

Figure 10:
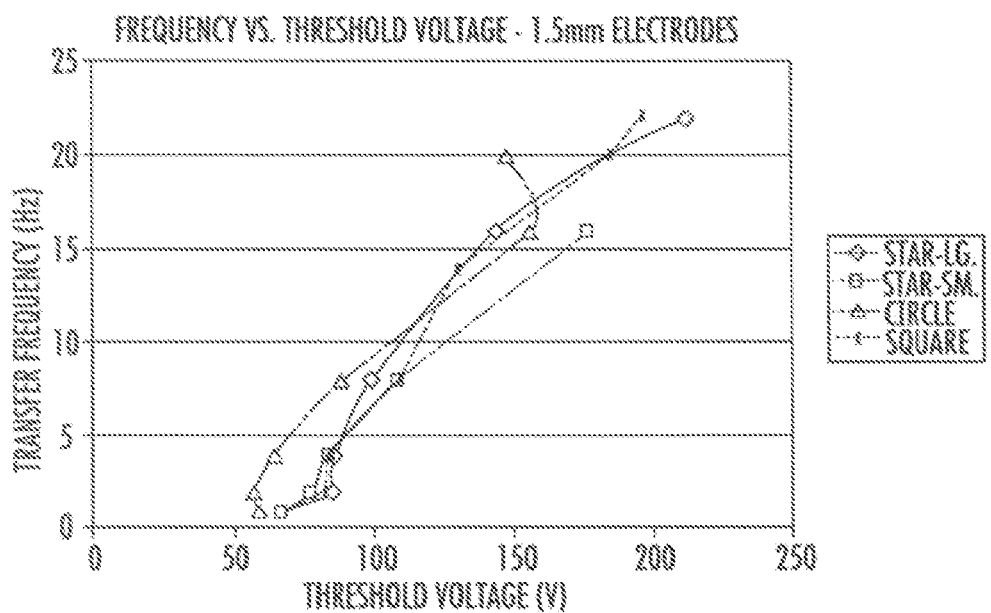
FIG. 10 is a graph depicting droplet transport characteristics (frequency vs. threshold voltage) of different shaped 1.5 mm electrodes in accordance with the present subject matter.
Figure 11:
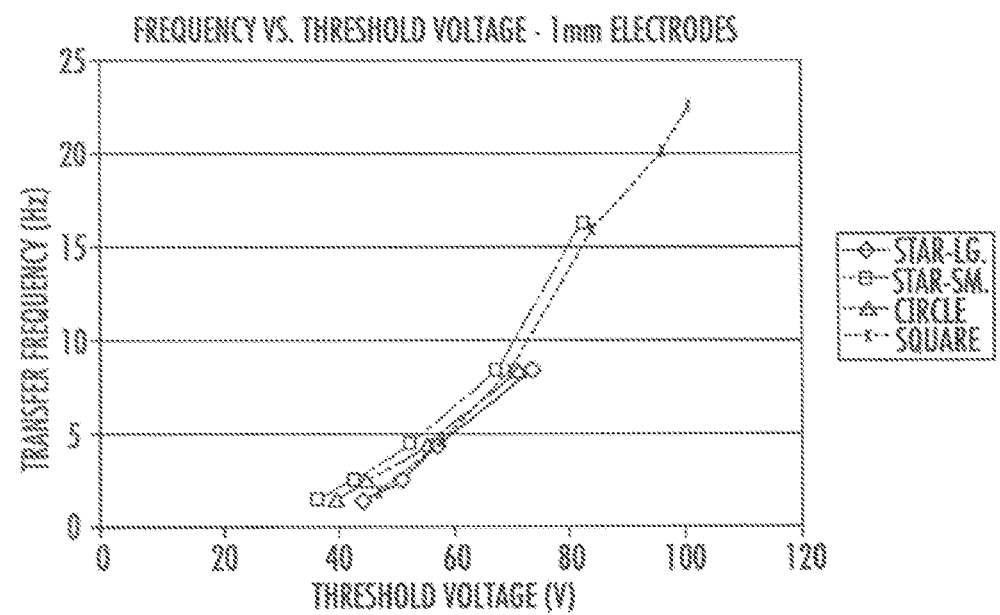
FIG. 11 is a graph depicting droplet transport characteristics (frequency vs. threshold voltage) of different shaped 1.0 mm electrodes in accordance with the present subject matter.

For each electrode size and shape the maximum rate at which droplets could be transported between adjacent control electrodes was determined as a function of the applied voltage, as shown in FIGS. 10 and 11. Droplets were successfully transported at voltages less than 40 V (for 1.0 mm electrode size) with transport speed increasing with voltage beyond that threshold. Higher voltages were required for droplet actuation than previously reported in other systems because of the use of the thicker soldermask insulator. For instance, the soldermask insulation is approximately 16 times thicker than the insulation used with previous microfabricated devices, and therefore approximately four (4) times as much voltage is required owing to the electrostatic energy ($½CV^2$) dependence of the transport mechanism.

As expected, beyond the initial threshold voltage, the speed of transport and consequently the maximum speed at which the droplet could be switched increased with voltage. The range of voltage tested was from roughly 0-200 V for the 1.5 mm electrodes and 0-100 V for the 1.0 mm electrodes, and droplet transport rates up to 24 Hz were observed. The resulting test curves exhibited an expected general shape—the higher the voltage applied the higher the possible transfer frequency. However, the curves for the 1.5 mm electrodes (FIG. 10) were not very smooth and there appears to be a significant effect of the shape of the electrode. Alternatively, the curves for the 1.0 mm electrodes (FIG. 11) are quite predictable and do not exhibit large dependence on electrode shape. In addition, there was a scaling effect where the threshold voltages of the 1.0 mm electrodes were 10-20 V lower than the 1.5 mm electrodes at corresponding frequencies.

Figure 12:
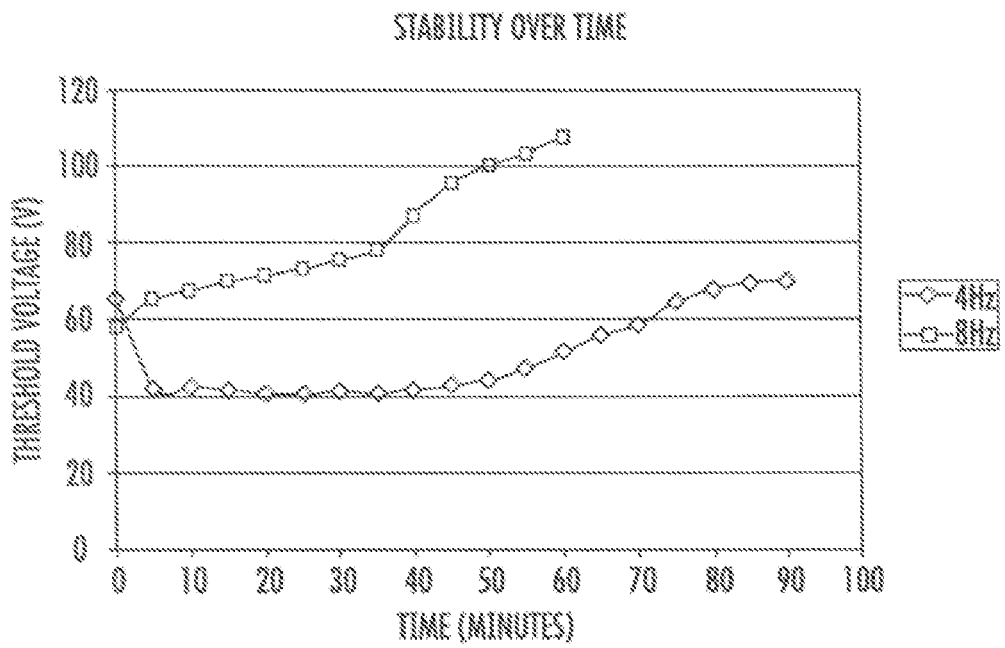
FIG. 12 is a graph depicting voltage stability of droplet transport over time in accordance with the present subject matter.

As shown graphically in FIG. 12, a further test was performed to determine the stability of droplet transport over time. A droplet was programmably cycled across four 1.5 mm square electrodes at the minimum voltage required to sustain transport at a switching frequency of either 4 Hz or 8 Hz. At five minute intervals the minimum voltage for continuous transport was tested and adjusted. The tests which were performed for an hour or more demonstrate a general trend of increasing voltage requirement over time which is presumably due to degradation of the insulator and contamination of the insulator surface. However, in each case over 20,000 cycles of droplet transport were performed during the experiment.

Figure 13:
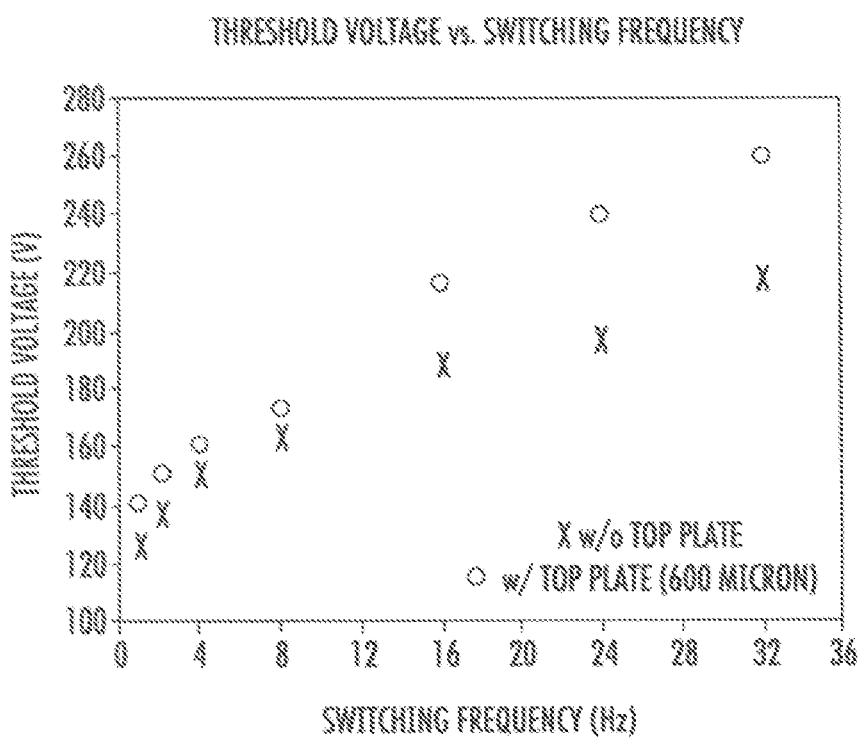
FIG. 13 is a graph depicting minimum voltage requirements for droplet transport at a given switching frequency in accordance with the present subject matter.

With reference to the graph shown in FIG. 13, tests were also conducted to determine the minimum voltage requirements for droplet transport at a given switching frequency. Digital microfluidic chips for both an open (i.e., co-planar without a top plate) and a confined (i.e., bi-planar with a top plate) structure on a PCB were used (see FIGS. 1B and 4B, respectively). Electrodes (1.5×1.5 mm$^2$) were patterned in copper to a final thickness of ~25 µm. 150 µm via holes were drilled into each electrode to provide electrical contacts to the backside of the board. Grounding rails were patterned alongside all the drive electrodes to provide a continuous ground connection to the droplets, and a liquid photoimageable (LPI) solder mask (~17 µm) was patterned to act as an insulator, exposing only the rails. As the only post-processing step, TEFLON® AF was brush-coated to render the surface hydrophobic. Droplets of a polarizable and conducting liquid (1M KCl) were transported in both the open (co-planar) and confined (bi-planar) systems. For the open system, each droplet was 6 µl in volume and a small drop of silicone oil (2 µl) was added and appeared to surround the droplet. For the confined system, the volume of each droplet was 2.5 µl, and the entire chip was filled with silicone oil to facilitate transport.

The minimum actuation voltages required to successfully transport droplets were measured for each system at switching frequencies ranging from 1 to 32 Hz. As shown graphically in FIG. 13, the operating voltages for droplets in the confined (bi-planar) and open (co-planar) systems ranged from 140-260V and 125-220V, respectively, depending on the switching frequency of the droplets. This appears to suggest that droplet actuation is facilitated by the absence of a confining top plate, possibly due to the reduced drag experienced by the unconfined droplet. Electrolysis of the droplets, typically due to improper coverage of the insulator, was not observed using LPI solder mask as an insulator up to the maximum tested voltage of 350V. Insulator charging, however, was experienced beyond 300V.

Figure 14:
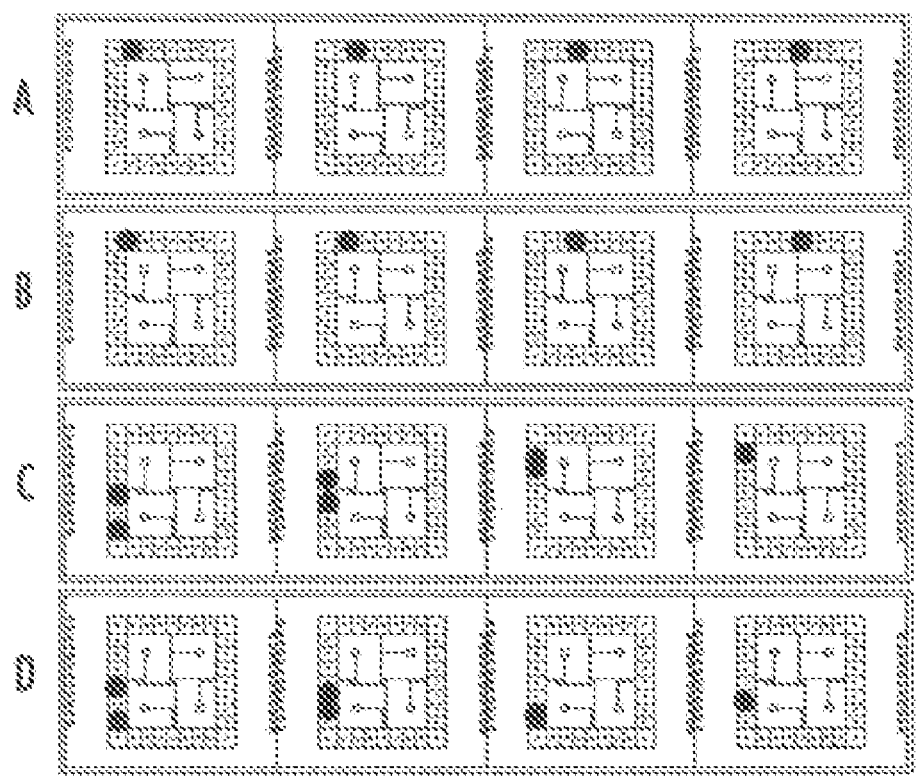
FIGS. 14A-14D are photographs depicting time-lapsed images demonstrating droplet transport and mixing in accordance with the present subject matter.

Referring to FIGS. 14A-14D, top views of various sequences of time-lapsed images demonstrating droplet transport and mixing are shown. FIGS. 14A-14B depict droplet transport and mixing, respectively, for droplets confined by a top plate (600 µm) (bi-planar). FIGS. 14C-14D depict droplet transport and mixing, respectively, for droplets in an open system (co-planar). Mixing was performed at a switching frequency of 8 Hz and was completed within 5 seconds for two 2.5 µl "confined" droplets, and within 1.8 seconds for two 6 µl droplets in an "open" system. Thus, the mixing rates (volume per unit time) observed in the open (co-planar) system is nearly seven times greater than in the confined system (bi-planar). This improved mixing may be attributed to increased circulation experienced within the thicker droplet, as circulation has previously been shown to worsen as droplets get thinner.

References

The references listed below are incorporated herein by reference to the extent that they supplement, explain, provide a background for or teach methodology, techniques and/or processes employed herein. All cited patent documents and publications referred to in this application are herein expressly incorporated by reference.

M. G. Pollack, R. B. Fair, and A. D. Shenderov, "Electrowetting-based actuation of liquid droplets for microfluidic actuation," *Appl. Phys. Lett.*, vol. 77, pp. 1725-1726 (2000).

V. Srinivasan, V. K. Pamula, and R. B. Fair, "An integrated digital microfluidic lab-on-a-chip for clinical diagnostics on human physiological fluids," Lab Chip, 4(4), 310, (2004)

B. Berge, and J. Peseux, "Variable focal lens controlled by an external voltage: An application of electrowetting," *The European Physical Journal E*, vol. 3, p. 159 (2000).

M. W. J. Prins, W. J. J. Welters, and J. W. Weekamp, "Fluid control in multichannel structures by electrocapillary pressure," *Science*, vol. 291, pp. 277-280 (2001).

T. Merkel, L. Pagel, and H. W. Glock, "Electric fields in fluidic channels and sensor applications with capacitance," *Sensors and Actuators A*, vol. 80, pp. 1-7 (2000).

A. Wego, and L. Pagel, "A self-filling micropump based on PCB technology," *Sensors and Actuators A*, vol. 88, pp. 220-226 (2001).

C. Laritz, and L. Pagel, "A microfluidic pH-regulation system based on printed circuit board technology," *Sensors and Actuators A*, vol. 84, pp. 230-235 (2000).

Li et al., "Development of PDMS-based Microfluidic Device for Cell-based Assays," *Chemical Journal of Chinese Universities*, vol. 25, no. 1, pp 4-6 (2004).

A. Wego, S. Richter, L. Pagel, "Fluidic microsystems based on printed circuit board technology," *Journal of Micromechanics and Microengineering*, vol. 11, no. 5, pp. 528-531 (September 2001).

A. Wego, H. W. Glock, L. Pagel, and S. Richter, "Investigations on thermo-pneumatic volume actuators based on PCB technology," *Sensors and Actuators A-Physical*, vol. 93, no. 2, pp. 95-102 (Sep. 30, 2001).

A. Wego and L. Pagel, "A self-filling micropump based on PCB technology," *Sensors and Actuators A-Physical*, vol. 88, no. 3, pp. 220-226 (Mar. 5, 2001).

C. Laritz and L. Pagel, "A microfluidic pH-regulation system based on printed circuit board technology," *Sensors and Actuators A-Physical*, vol. 84, no. 3, pp. 230-235 (Sep. 1, 2000).

T. Merkel, M. Graeber, and L. Pagel, "A new technology for fluidic microsystems based on PCB technology," *Sensors and Actuators A-Physical*, vol. 77, no. 2, pp. 98-105 (Oct. 12, 1999).

N. T. Nguyen and X. Y. Huang, "Miniature valveless pumps based on printed circuit board technique," *Sensors and Actuators A-Physical*, vol. 88, no. 2, pp. 104-111 (Feb. 15, 2001).

C. W. Li, C. N. Cheung, J. Yang, C. H. Tzang, and M. S. Yang, "PDMS-based microfluidic device with multi-height structures fabricated by single-step photolithography using printed circuit board as masters," *Analyst*, vol. 128, no. 9, pp. 1137-1142 (2003).

A. P. Sudarsan and V. M. Ugaz, "Printed circuit technology for fabrication of plastic-based microfluidic devices," *Analytical Chemistry* vol. 76, no. 11, pp. 3229-3235 (Jun. 1, 2004).

G. Jobst, I. Moser, P. Svasek, M. Varahram, Z. Trajanoski, P. Wach, P. Kotanko, F. Skrabal, and G. Urban, "Mass producible miniaturized flow through a device with a biosensor array," *Sensors and Actuators B-Chemical*, vol. 43, pp. 121-125 (September 1997).

M. A. Unger, H. P. Chou, T. Thorsen, A. Scherer, S. R. Quake, "Monolithic Microfabricated Valves and Pumps by Multilayer Soft Lithography," *Science*, vol. 288, pp. 113-116 (2000).

A. R. Wheeler, H. Moon, C. A. Bird, R. R. Loo, C. J. Kim, J. A. Loo, R. L. Garrell, "Digital microfluidics with in-line sample purification for proteomics analyses with MALDI-MS," *Analytical Chemistry*, vol. 77, no. 2, pp. 534-40 (2005).

J. A. Schwartz, J. V. Vykoukal and P. R. C. Gascoyne, "Droplet-based chemistry on a programmable micro-chip," *Lab on a Chip*, vol. 4, no. 1, pp. 11-17 (2004).

Y. Tan, J. S. Fisher, A. I. Lee, V. Cristini and A. P. Lee, "Design of microfluidic channel geometries for the control of droplet volume, chemical concentration, and sorting," *Lab on a Chip*, vol. 4, no. 4, pp. 292-298 (2004).

J. D. Tice, A. D. Lyon, and R. F. Ismagilov, "Effects of viscosity on droplet formation and mixing in microfluidic channels," *Analytica Chimica Acta*, vol. 507, pp. 73-77 (2004).

T. Merkel, L Pagel, H. Glock, "Electric fields in fluidic channels and sensor applications with capacitance", *Sensors and Actuators*, vol. 80, pp. 1-7 (2000).

G. Medoro, N. Manaresi, A. Leonardi, L. Altomare, M. Tartagni and R. Guerrieri, "A Lab-on-a-Chip for Cell Detection and Manipulation", *IEEE Sensors Journal*, vol. 3, pp. 317-325 (2003).

L. Altomare, M. Borgatti, G. Medoro, M. Manaresi, M. Tartagni, R. Guerrieri and R. Gambari, "Levitation and Movement of Human Tumor Cells Using a Printed Circuit Board Device Based on Software-Controlled Dielectrophoresis", *Biotechnology and Bioengineering*, vol. 82, pp. 474-479 (2003).

Conclusion

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of amplifying DNA comprising:
   (a) providing a sample solution comprising DNA on a printed circuit board substrate comprising an array of electrodes for transporting droplets on the substrate, and a dielectric coating atop the electrodes, wherein the printed circuit board substrate is provided as part of a sandwich structure, the sandwich structure further comprising:
       (i) a top plate parallel to the printed circuit board substrate and forming a gap between the top plate and the printed circuit board substrate;
       (ii) a seal between the top plate and the printed circuit board substrate; and
       (iii) oil in the gap; and
   (b) amplifying the DNA on the printed circuit board substrate, wherein the amplifying is achieved by thermocycling wherein the amplifying is accomplished in a droplet in the oil in the gap.

* * * * *